United States Patent
Kaumaya et al.

(10) Patent No.: US 7,220,822 B2
(45) Date of Patent: May 22, 2007

(54) CD28 MIMETICS FOR BLOCKING T CELL MEDIATED IMMUNE REACTIONS

(75) Inventors: Pravin T. P. Kaumaya, Westerville, OH (US); Caroline C. Whitacre, Columbus, OH (US); Mythily Srinivasan, Columbus, OH (US)

(73) Assignee: The Ohio State University, Columbus, OH (US)

( * ) Notice: Subject to any disclaimer, the term of this patent is extended or adjusted under 35 U.S.C. 154(b) by 752 days.

(21) Appl. No.: 09/990,574

(22) Filed: Nov. 21, 2001

(65) Prior Publication Data

US 2002/0156008 A1 Oct. 24, 2002

Related U.S. Application Data

(60) Provisional application No. 60/252,744, filed on Nov. 22, 2000, provisional application No. 60/250,984, filed on Dec. 4, 2000.

(51) Int. Cl.
*C07K 7/08* (2006.01)
*C07K 14/00* (2006.01)

(52) U.S. Cl. ............... 530/300; 530/324; 530/325; 530/326; 530/345

(58) Field of Classification Search ............... 530/300, 530/324, 325, 326, 335, 337
See application file for complete search history.

(56) References Cited

U.S. PATENT DOCUMENTS 5,773,253 A * 6/1998 Linsley et al. ............ 435/69.7
2002/0182727 A1* 12/2002 Freeman et al. ............ 435/325
2004/0229790 A1* 11/2004 Tezuka et al. ............ 514/12

OTHER PUBLICATIONS

Altwood, Science, 2000, vol. 290, pp. 471-473.*
Skolnick et al., Trends in Biotech, 2000, vol. 18, pp. 34-39.*
Metzler et al., Nature Structural Biol. 1997; 4:527-531.*
"Costimulatory Blockade by CD28 Peptide Mimics: Suppression of Experimental Autoimmune Encephalomyelitis" by Srinivasan, et al., *American Peptide Society*, Jun. 9, 2001, pp. 654-655.
"A CD28 CDR3 peptide analog inhibits CD4+ T-cell proliferation *in vitro*" by Srinivasan, et al., *Peptides for the New Millenium* (Eds. Fields, G.B., Tam T.P. and Barany) Kluwer Academic Publishers, Dordrecht, Netherlands, Jun. 26, 1999, pp. 689-690.
"A Retro-Inverso Peptide Mimic of CD28 Encompassing the MYP-PPY Motif Adopts a Polyproline Type II Helix and Inhibits Encephalitogenic T Cells In Vitro" by Srinivasan, *The Journal of Immunology*, vol. 167(1), Jul. 1, 2001, pp. 578-585.
"Suppression of Experimental Autoimmune Encephalomyelitis Using Peptide Mimics of CD28" by Srinivasan, et al., *Journal of Immunology*, 2002, 169: 2180-2188.

* cited by examiner

*Primary Examiner*—Phillip Gambel
*Assistant Examiner*—Ilia Ouspenski
(74) *Attorney, Agent, or Firm*—Calfee, Halter & Griswold LLP

(57) ABSTRACT

Agents for blocking T cell-mediated immune reactions are provided. Such agents are peptides, referred to as "CD28 peptide mimetics", of from 15 to 30 amino acids in length. The CD28 peptide mimetics comprise the hexapeptide motif 'MYPPPY', SEQ ID NO: 1, or a retro-inverso isomer thereof. The CD28 peptide mimetics further comprise flanking sequence at the amino and carboxyl terminus of the hexapeptide motif. Methods for treating subjects with T cell mediated autoimmune diseases or disorders are also provided. Such methods comprise administering one or more of the CD28 peptide mimetics to a subject with such a disease or disorder.

7 Claims, 10 Drawing Sheets

Wavelength (nM)

Wavelength (nM)

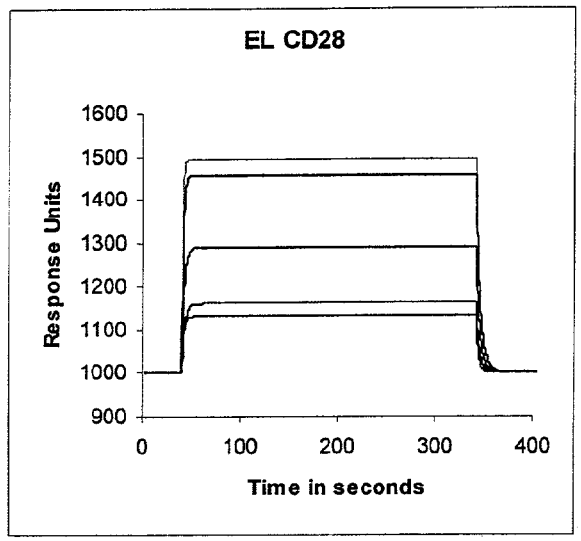
Fig. 2A
Fig. 2B
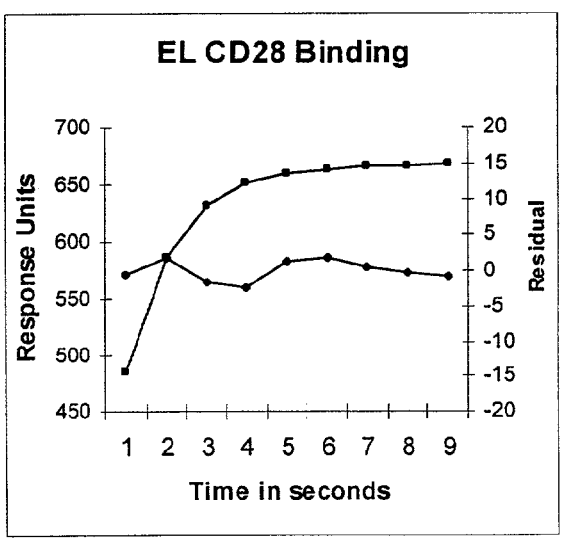
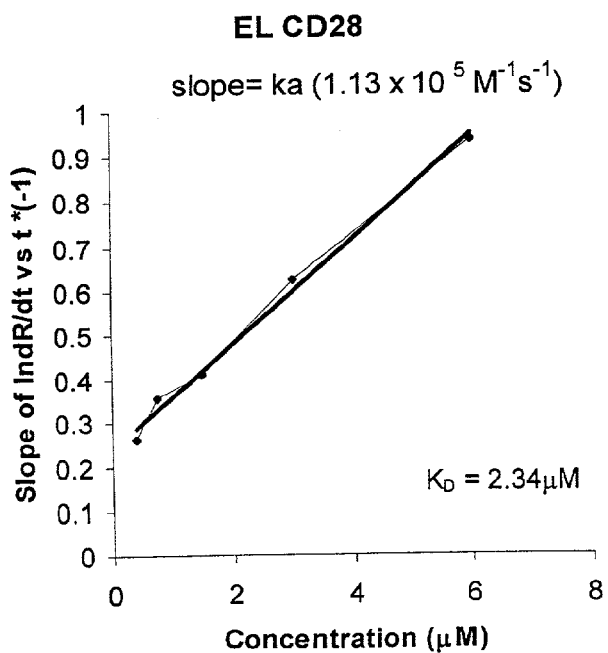
Fig. 2C

SEQUENCE LISTING

```
<160> NUMBER OF SEQ ID NOS: 12

<210> SEQ ID NO 1
<211> LENGTH: 6
<212> TYPE: PRT
<213> ORGANISM: Homo sapiens

<400> SEQUENCE: 1

Met Tyr Pro Pro Pro Tyr
1               5

<210> SEQ ID NO 2
<211> LENGTH: 6
<212> TYPE: PRT
<213> ORGANISM: Homo sapiens

<400> SEQUENCE: 2

Tyr Pro Pro Pro Tyr Met
1               5

<210> SEQ ID NO 3
<211> LENGTH: 8
<212> TYPE: PRT
<213> ORGANISM: Homo sapiens

<400> SEQUENCE: 3

Phe Met Tyr Pro Pro Pro Tyr Leu
1               5

<210> SEQ ID NO 4
<211> LENGTH: 11
<212> TYPE: PRT
<213> ORGANISM: Homo sapiens
```

```
<400> SEQUENCE: 4

Leu Tyr Pro Pro Pro Tyr Met Phe Glu Ile Lys
1               5                   10

<210> SEQ ID NO 5
<211> LENGTH: 20
<212> TYPE: PRT
<213> ORGANISM: Homo sapiens

<400> SEQUENCE: 5

Lys Ile Glu Phe Met Tyr Pro Pro Pro Tyr Leu Asp Asn Glu Arg Ser
1               5                   10                  15

Asn Gly Ile Glu
            20

<210> SEQ ID NO 6
<211> LENGTH: 20
<212> TYPE: PRT
<213> ORGANISM: Homo sapiens

<400> SEQUENCE: 6

Glu Ile Gly Asn Ser Arg Glu Asn Asp Leu Tyr Pro Pro Pro Tyr Met
1               5                   10                  15

Phe Ile Glu Lys
            20

<210> SEQ ID NO 7
<211> LENGTH: 18
<212> TYPE: PRT
<213> ORGANISM: Homo sapiens

<400> SEQUENCE: 7

Leu Ser Leu Ser Leu Ser Met Tyr Pro Pro Tyr Leu Ser Leu Ser
1               5                   10                  15

Leu Ser

<210> SEQ ID NO 8
<211> LENGTH: 27
<212> TYPE: PRT
<213> ORGANISM: Homo sapiens

<400> SEQUENCE: 8

Leu Ser Leu Ser Leu Ser Lys Glu Ile Phe Met Tyr Pro Pro Pro Tyr
1               5                   10                  15

Leu Asp Asn Glu Ser Leu Ser Leu Ser Leu Ser
            20                  25

<210> SEQ ID NO 9
<211> LENGTH: 18
<212> TYPE: PRT
<213> ORGANISM: Homo sapiens

<400> SEQUENCE: 9

Ser Leu Ser Leu Ser Leu Tyr Pro Pro Pro Tyr Met Ser Leu Ser Leu
1               5                   10                  15

Ser Leu

<210> SEQ ID NO 10
<211> LENGTH: 25
<212> TYPE: PRT
<213> ORGANISM: Homo sapiens
```

-continued

```
<400> SEQUENCE: 10

Ser Leu Ser Leu Ser Leu Glu Asn Asp Leu Tyr Pro Pro Tyr Met Phe
1               5                   10                  15

Ile Glu Lys Ser Leu Ser Leu Ser Leu
            20                  25

<210> SEQ ID NO 11
<211> LENGTH: 20
<212> TYPE: PRT
<213> ORGANISM: Homo sapiens

<400> SEQUENCE: 11

Lys Ile Glu Phe Met Tyr Pro Pro Pro Tyr Leu Asp Asn Glu Arg Ser
1               5                   10                  15

Asn Gly Thr Ile
            20

<210> SEQ ID NO 12
<211> LENGTH: 20
<212> TYPE: PRT
<213> ORGANISM: Homo sapiens

<400> SEQUENCE: 12

Ile Thr Gly Asn Ser Arg Glu Asn Asp Leu Tyr Pro Pro Pro Tyr Met
1               5                   10                  15

Phe Glu Ile Lys
            20
```

CD28 MIMETICS FOR BLOCKING T CELL MEDIATED IMMUNE REACTIONS

This application claims priority to U.S. Provisional Application 60/252,744 filed Nov. 22, 2000 and U.S. Provisional Application 60/250,984 filed Dec. 4, 2000, both of which are incorporated herein in their entirety.

BACKGROUND

The present invention relates to agents and methods for blocking deleterious T cell mediated immune reactions. Such reactions occur in autoimmune diseases, such as for example, multiple sclerosis (MS), rheumatoid arthritis, systemic lupus erythematosis, psoriasis, diabetes, and allergies. Such reactions also occur during rejection of transplants.

Two types of signals are required for T cell activation and proliferation. The first, which gives specificity to the immune response, involves an interaction between the T-cell receptor/CD3 complex and an antigenic peptide presented by major histocompatibility complex (MHC) class I or class II proteins on the surface of an antigen-presenting cell (APC). The second type of signal, called a costimulatory signal, involves interaction between receptor-ligand pairs expressed on the surface of APCs and T cells. Antigenic stimulation in the absence of costimulation mechanisms induces a state of unresponsiveness or anergy and eventual cell death by apoptosis in the responding T cells. Thus, antigenic stimulation in the presence of costimulation prevents anergy and cell death, thereby promoting cell survival.

CD 28 is one of the principal T cell costimulatory receptors. CD28 binds APC costimulatory ligands B7.1 (CD80) and B7.2(CD86). CD28 is a transmembrane homodimer that is constitutively expressed on 90% of mammalian CD4+ T cells. Upon binding to the B7 family of molecules, CD28 delivers a powerful costimulatory signal for T cell activation and clonal expansion. Engagement of CD28 by its ligands B7-1 or B7-2 on the surface of APCs initiates a signaling cascade culminating in cytokine production and expansion of specific T-cells.

T cells also express cytotoxic-T-lymphocyte antigen 4, CTLA-4 (CD152), a close relative of CD28. In contrast to CD28, CTLA-4 is not expressed by naive T cells but is rapidly induced after T cell activation. Analogous to CD28, CTLA-4 also binds the B-7 family of molecules, albeit with higher avidity than CD28. Engagement of CTL4 with the B7 ligands transmits a negative signal to the T cells, thus terminating the immune response.

The critical role played by the B7/CD28:CTLA-4 costimulatory interaction in determining the fate of immune responses (activation vs anergy/apoptosis) makes it an attractive target for therapeutic immunomodulation in a wide range of autoimmune diseases. Recently, it has been shown that administration of monoclonal antibodies to B7 molecules and CTLA-4 Ig fusion protein ameliorate autoimmune diseases in various animal models, including (EAE) an animal model for MS, diabetes and systemic lupus erythematosis. However, these results depend upon the timing of antibody administration. For example, CTLA-4 Ig was not effective in blocking already established EAE, and anti B7-2 mAB and anti CTLA-4 mAB exacerbate the disease. Moreover, the value of such antibodies as effective therapeutic agents is limited by virtue of their inherent immunogenicity and poor penetration across tissue barriers.

Accordingly, it is desirable to have additional methods and agents which can be used to block deleterious T-cell mediated immune reaction and to ameliorate the symptoms of diseases and disorders associated with such reactions.

SUMMARY OF THE INVENTION

The present invention provides new agents for blocking T cell-mediated immune reactions. Such agents are peptides, referred to hereinafter as "CD28 peptide mimetics", of from 15 to 30 amino acids in length. The CD28 peptide mimetics comprise the hexapeptide motif 'MYPPPY' (SEQ ID NO: 1) or a retro-inverso isomer thereof. The CD 28 peptide mimetics further comprise flanking sequence at the amino and carboxyl terminus of the hexapeptide motif. Such flanking sequence permit the CD28 peptide mimetic to assume a polyproline II (PPII) conformation when placed in water or a buffered solution at physiological pH and a temperature of about 25° C.

The present invention relates to methods for treating subjects with T cell mediated autoimmune diseases or disorders. Such methods comprise administering one or more of the CD 28 peptide mimetics to a subject which has such disease or disorder.

The present invention also relates to a method of blocking activation and proliferation of CD4+ cells. The method comprises contacting such cells with one or more of the present CD 28 peptide mimetics.

BRIEF DESCRIPTION OF THE FIGURES

FIG. 1: (A) CD spectra of end group blocked L CD28 (ELCD28) and retro-inverso CD28 peptide (RICD28) at 400 μM in PBS, 50% TFE at 25° C. and, (B) at 35° C. Mean residue ellipticity (θ) is expressed in degrees $cm^2$ $dmol^{-1}$.

FIG. 2: Affinity and kinetics of EL CD28 peptide binding to CD80-Ig. (A) A range of EL CD28 peptide concentrations (375 nM to 18 μM) were injected for 300 s at 10 μl/min through a flow cell with CD80-Ig (1488 RU) or no protein (control) immobilized. (B) Injection phase analysis of a representative binding curve and the residual following injection of EL CD28 peptide (6 μM) over CD80-Ig immobilized and control flow cell. (C) A plot of (dR/dt) against RU was calculated from the sensograms and the slope of this plot was plotted against concentration of ELCD28 peptide. The association rate constant of the interaction between EL CD28 and CD80-Ig, as measured from the slope of this plot, is indicated. The dissociation rate constant is obtained from the intercept. The data yields a $K_d$ of 2.34 μM for the interaction between EL CD28 peptide and CD80-Ig.

FIG. 3: Affinity and kinetics of RI CD28 peptide binding to CD80-Ig. (A) A range of RICD28 peptide concentrations (375 nM to 18 μM) were injected for 300 s at 10 μl/min through a flow cell with CD80-Ig (1512 RU) or no protein (control) immobilized. (B) Injection phase analysis of a representative binding curve and the residual, following injection of RI CD28 peptide (6 μM) over CD80-Ig i m mobilized and control flow cell. (C) A plot of (dR/dt) against RU was calculated from the sensograms and the slope of this plot was plotted against the concentration of RICD28 peptide. The association rate constant of the interaction between RI CD28 and CD80-Ig, as measured from the slope of this plot, is indicated. The dissociation rate constant is obtained from the intercept. The data yields a $K_d$ of 2.53 μM for the interaction between EL CD28 peptide and CD80-Ig.

FIG. 4: Competitive kinetics between CD28 APR and CD28-Ig for binding immobilized CD80-Ig. (A) An overlay of sensograms obtained from injection of a mixture of CD28-Ig at constant concentration (3.2 μM) and EL CD28 peptide at varying concentration (375 µM to 6 µM) at 10 µl/min over a flow cell with bound CD80-Ig (322 RU). The top curve represents the binding of CD28-Ig alone in the absence of competing peptide. The response of CD28-Ig binding decreases with increasing concentration of EL CD28 peptide. (B) An overlay of sensograms obtained from injection of a mixture of CD28-Ig at constant concentration (3.2 µM), and RI CD28 peptide at varying concentration (375 nM to 6 µM) at 10 µl/min over a flow cell with bound CD80-Ig (338.6 RU). The top curve represents the binding of CD28-Ig alone in the absence of competing peptide.

Figure 5A:
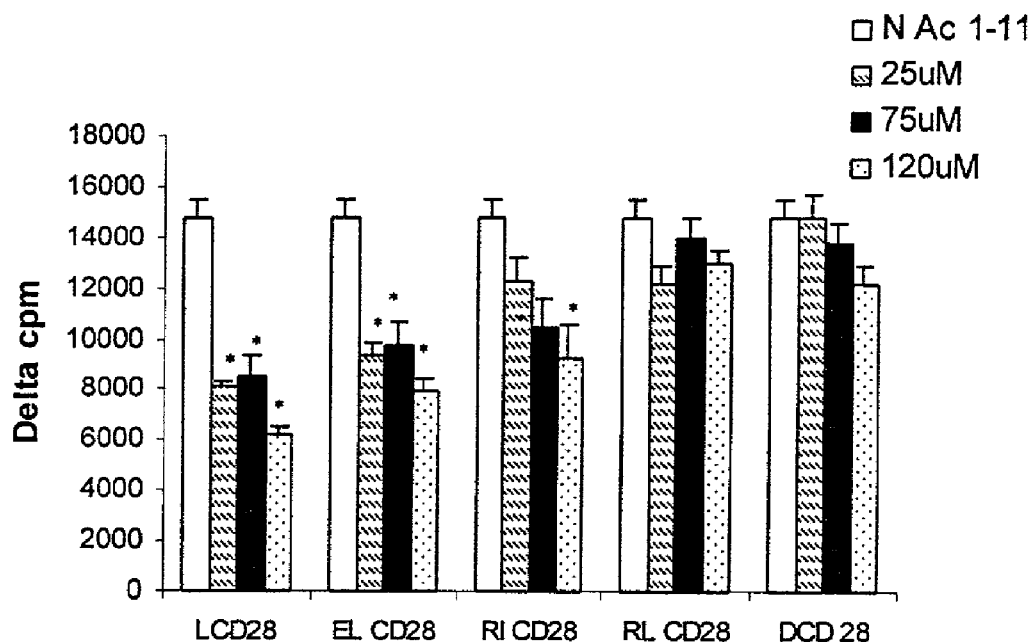
Figure 5B:
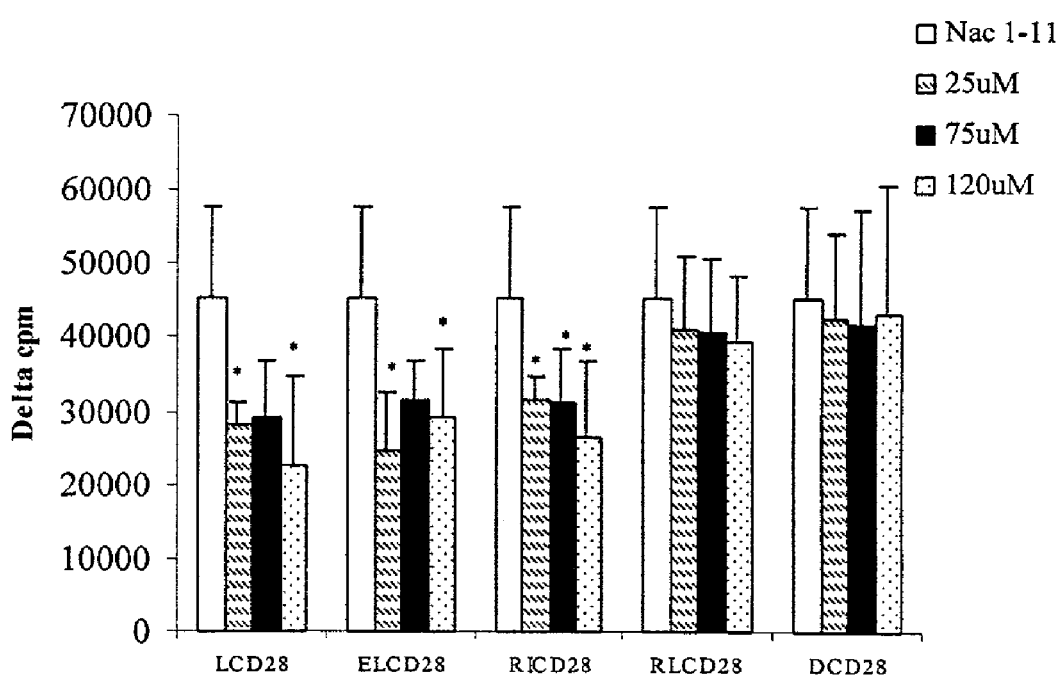

FIG. 5: Antigen-specific T-cell proliferative responses of lymph node cells and splenocytes from MBP peptide-specific TCR transgenic mice that carry a Vα4 Vβ8.2 TCR treated with CD28 peptides. Single cell suspensions of CD4+ T cells isolated from the (A) lymph nodes and (B) spleen ($5 \times 10^4$ cells /well) were stimulated with the encephalitogenic peptide of MBP, NAc 1-11 (10 µg/ml) and cultured for a total of 72 hr (including an 18 hr pulse with $H^3$ thymidine) in the presence of varying concentrations of CD28 peptide analogues as shown. Data represents mean thymidine uptake and is plotted as delta cpm±SE. Results are mean of three different experiments. Proliferative responses of CD4+ LNC and spleen cells treated with L CD28, end group blocked CD28 and retro-inverso CD28 at all concentrations used were significantly less than untreated and control peptide (Reverse L CD 28 and D CD 28) treated cells *=p<0.01 by ANOVA.

Figure 6:
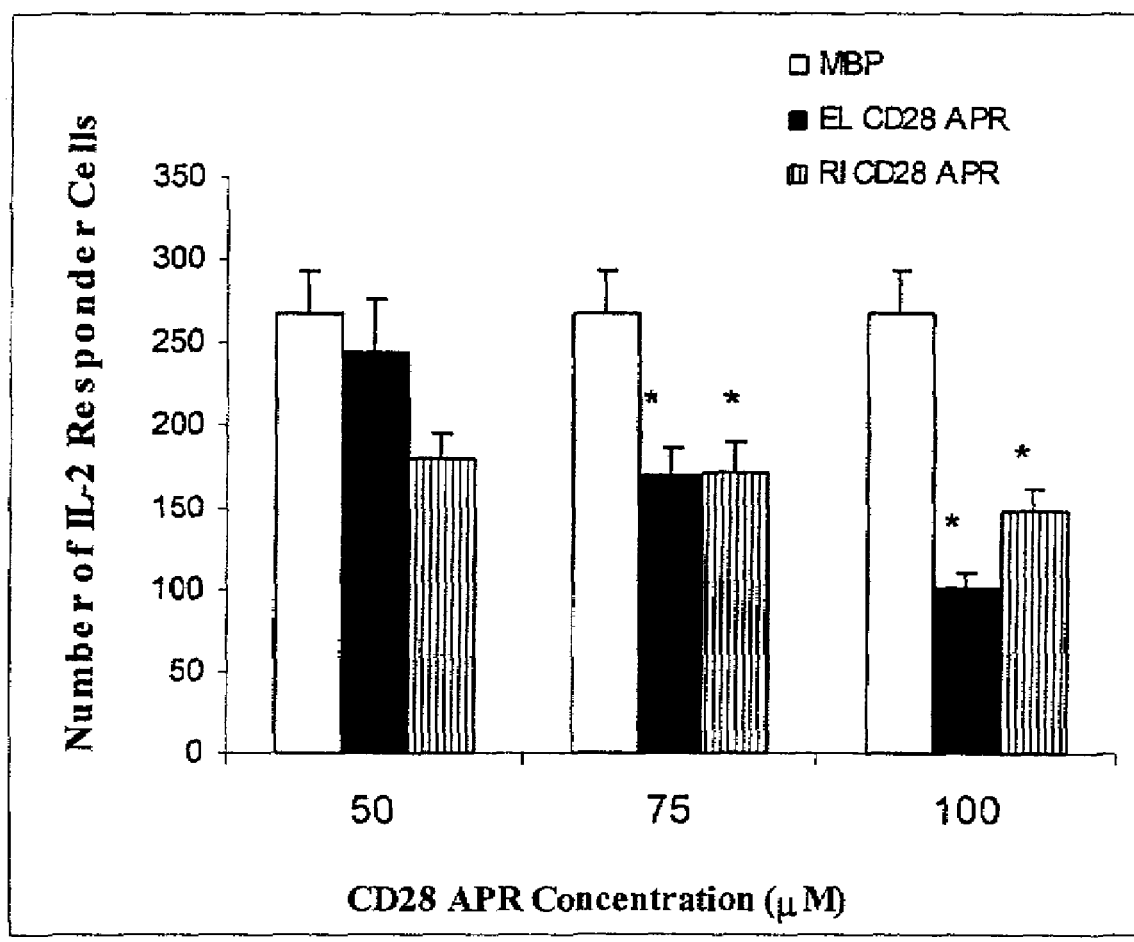

FIG. 6: Fewer cells secrete IL-2 when stimulated in the presence of CD28 APR. CD4+ T cells were isolated from the pooled lymph nodes of Vβ8.2 Vα 4 TCR transgenic mice and stimulated with 10 µg/ml of NAc 1-11 peptide of MBP either alone or in the presence of the specified concentrations CD28 APR and assayed by ELISASPOT. Significant decrease in the number of NAc1-11 responders was observed following treatment with EL CD28 and RI CD28 @75 µM and 100 µM concentrations. Results are representative of two experiments *=p<0.05 by one way ANOVA FIG. 7: (A) CD28 synthetic peptide treatment increases apoptosis of CD4+ T cells in vitro. $5 \times 10^5$ CD4+ T cells were isolated from the pooled lymph nodes of Vβ8.2 Vα 4 TCR transgenic mice and stimulated with 10 µg/ml of NAc 1-11 peptide of MBP either alone or in the presence of the specified concentrations CD28 APR. Lymph node cells were harvested after 48 hrs and apoptotic cells among Vβ8.2+ cells were detected by the TUNEL methods and analyzed by flow cytometry. The data shown is the average results from three experiments. Significant increase in the percentage of apoptotic cells was observed following treatment with 150 µM EL CD28 and 75 µM or 150 µM RI CD28 APR. Lymph node cells alone or when treated with the CD28 peptides in the absence of antigen showed maximum apoptosis (Data not shown). *p<0.01 by one way ANOVA. Representative histograms showing increase in FITC conjugated TUNEL positive cells in cultures treated with 120 µM EL CD28 or RI CD28 are shown in (B) and (C) respectively.

FIG. 8: Injection of synthetic CD28 peptide analogues inhibits development of clinical EAE and attenuates established EAE. B10.PL mice were immunized with GP-MBP in CFA and injected pertussis toxin i.p. on day 0 and 2. The data are presented as the mean clinical score in each group on different days of observation. Animals received a single i.v. injection of 500 µg of ELCD28(n=10) or RI CD28(n=10) peptides or control [LCD28(n=12), RLCD28 (n=6) and D CD28(n=6)] peptides or PBS (n=12) on the day of immunization (A) or on day 14 post-immunization (B).Data represent the means of pooled data from two separate experiments.

DETAILED DESCRIPTION OF THE INVENTION

The present invention provides peptides, i.e. CD28 peptide mimetics and compositions containing such peptides, which are useful for blocking or inhibiting activation and proliferation of T cells, particularly CD4+ cells.

The CD 28 peptide mimetics are from 15 to 30 amino acids, preferably from 17 to 25 amino acids, more preferably from 19 to 21 amino acids in length. The CD28 peptide mimetics comprise a hexapeptide with the following sequence: MYPPPY, SEQ ID NO: 1, or the retro-inverso isomer thereof, i.e., YPPPYM, SEQ ID NO: 2. The CD28 peptide mimetics further comprise flanking sequences, i.e. a plurality of amino acids, at the amino and a plurality of amino acids at carboxy termini of the hexapeptide motif. Preferably, the hexapeptide is sandwiched between two amphiphilic, anti-parallel right-twisted β strands. For optimum stability of the CD28 peptide mimetic, it is preferred that the antiparallel β strands be of the same length.

In those instances where the methionine is at the amino terminus of the hexapeptide, the CD 28 peptide mimetic, referred to hereinafter as "L" peptide mimetic, is comprised of levorotary amino acids. In those instances where the methionine is at the carboxy terminus of the hexapeptide, the CD 28 peptide mimetic, referred to hereinafter as a "D" peptide mimetic, is comprised of dextrorotary amino acids such that the D peptide mimetic is a topochemical equivalent of the corresponding L peptide mimetic. The retro-inverso modification of the L-peptide mimetic to produce a corresponding D peptide mimetic involves the reversal of all amide bonds within the peptide backbone. This is achieved by reversing the direction of sequence and inverting the chirality of each amino acid residue by using D-amino acids. The goal of this topochemical approach is to create an analog such that the reversed amide bonds in the D peptide mimetic retains both the planarity and conformational restrictions of peptide bonds (CONH) and the spatial orientation of side chains remains closely related to that of the corresponding L peptide mimetic. Advantageously, the D peptide mimetic is resistant to proteases that are present in mammals.

The amino and carboxy termini of the CD 28 peptide mimetics may be free or, preferably, end-blocked. When placed in water or a buffered solution having a pH of about 7.4, the CD 28 peptide mimetics adopt a PPII helical conformation. The secondary structure of the CD 28 peptide and the presence of a PPII helical conformation may be determined using a circular dichroism assay.

The CD28 peptide mimetics bind B7 molecules on APC's (Antigen Presenting Cells) with an affinity which, preferably is less than the affinity of CTLA-4 for these molecules. The CD 28 peptide mimetics bind B7 molecules with an affinity which is equivalent to the affinity of CD28 for these ligands. This property can be determined empirically using a competitive binding analysis. Alternatively, the relative affinity of the CD 28 peptide mimetic for B7 molecules can be estimated on the basis of $K_a$ and $K_d$ measurements.

The CD 28 peptide mimetic has a $K_d$ which is equivalent to the $K_d$ of CD28. The CD 28 peptide mimetic has a $K_d$, preferably, between 2 and 3 micromoles, more preferably, between 2.1 and 2.7 micromoles. Thus, the CD 28 peptide mimetic binds to the B71 ligand and the B7 2 ligand, which are also known as CD 80 and CD 86 respectively, with fast kinetics.

In certain embodiments, the L form of the CD28 peptide mimetic comprises the following sequence: FMYPPPYL, SEQ ID NO: 3. The corresponding D form of this peptide mimetic is the retro inverso isomer of this sequence. In certain embodiments, the D form of the CD 28 peptide mimetic comprises the sequence LYPPPYMFEIK, SEQ ID NO: 4. In one embodiment, the CD28 peptide mimetic is an L-peptide which comprises 20 L-amino acids, has the sequence KIEFMYPPPYLDNERSNGIE, SEQ ID NO: 5, and has free ends. In another embodiment, the peptide mimetic is an L-peptide which comprises 20 L-amino acids, has the sequence KIEFMYPPPYLDNERSNGIE, SEQ ID NO: 5 and has blocked ends; i.e., the lysine at the amino terminus is acetylated and the glutamic acid at the carboxy terminus is amidated. In a further embodiment, the peptide mimetic is a D-peptide which comprises 20 D-amino acids and has the sequence EIGNSRENDLYPPPYMFIEK, SEQ ID NO: 6, and has free ends. In another embodiment, the peptide mimetic is a D-peptide which comprises 20 D-amino acids and has the sequence EIGNSRENDLYPPPYMFIEK, SEQ ID NO: 6, wherein the aspartic acid residue at the amino terminus is acetylated and the lysine residue at the carboxy terminus is amidated. In certain embodiments of the L form of the CD28 peptide mimetic, flanking regions of the core hexapeptide comprise a repetitive LS sequence; while the flanking regions of the corresponding D form of the CD28 peptide mimetic comprise a repetitive SL sequence. Thus, the CD 28 peptide mimetic may comprise one of the following sequences LSLSLSMYPPPYLSLSLS, SEQ ID NO: 7,
LSLSLSKEIFMYPPPYLDNESLSLSLS, SEQ ID NO: 8,
SLSLSLYPPPYMSLSLSL SEQ ID NO: 9, and
SLSLSLENDLYPPYMFIEKSLSLSL, SEQ ID NO: 10.

The present CD 28 peptide mimetics also encompass peptides that are biologically equivalent variants of SEQ ID NO: 5, SEQ ID NO: 6, SEQ ID NO: 7, SEQ ID NO: 8, SEQ ID NO: 9, and SEQ ID NO: 10. A "biologically equivalent variant" as used herein, refers to a peptide whose amino acid sequence is similar but not identical to the amino acid sequence of one of these sequences, hereinafter referred to as the "reference" amino acid sequence, but does not have 100% identity with such reference sequence. Peptides which are biologically equivalent variants have an altered sequence in which one or more of the amino acids in the reference sequence other than the hexapeptide motif, i.e., in the flanking sequence, is substituted, or in which one or more amino acids are deleted from or added to one or both of the flanking sequences of the hexapeptide motif. Preferably the deletions and additions are located at the amino terminus, the carboxy terminus, or both, of one of the sequences shown above.

While it is possible to have nonconservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acid, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another. As a result of the alterations, such the biologically equivalent variant has flanking amino acid sequences which are at least 70% identical, preferably at least 80% identical, more preferably at least 90% identical to the flanking amino acid sequence of reference sequence. Variant sequences, which are at least 90% identical, have no more than 1 alteration, i.e., any combination of deletions, additions or substitutions, per 10 amino acids of the flanking amino acid sequence. Percent identity is determined by comparing the amino acid sequence of the variant with the reference sequence using MEGALIGN module in the DNA STAR program.

Peptides which are biologically equivalent variants of CD 28 peptide mimetics comprising SEQ ID NO: 5, SEQ ID NO: 6, SEQ ID NO: 7, SEQ ID NO: 8, SEQ ID NO: 9, and SEQ ID NO: 10 bind to B71 and B72 with an affinity that is less than CTLA-4 and comparable to CD28. Peptides which are biologically equivalent variants of CD 28 peptide mimetics comprising SEQ ID NO: 5, SEQ ID NO: 6, SEQ ID NO: 7, SEQ ID NO: 8, and SEQ ID NO: 9 have a $K_d$ which is between 2 and 3 micromoles.

The present invention also provides a method of treating the symptoms of a disease or disorder that involves a deleterious activation of T cells. Examples of such diseases are autoimmune diseases, such as MS, EAE which is the mouse model for MS, rheumatoid arthritis, and insulin-dependent diabetes mellitus. One example of another disorder that involves deleterious activation of T cells is rejection of an allograft transplant. Such method comprises administering a pharmaceutical composition, which comprises an L CD 28 peptide mimetic, a D CD 28 peptide mimetic or both to a subject in need of the same. As used herein, the term subject refers to a mammalian animal, preferably a human. By "treating" is meant ameliorating or tempering the severity of the disorder or the symptoms associated therewith. In such cases, as for example multiple sclerosis, the pharmaceutical composition is administered either when patients have clinical symptoms, or when a genetic mutation indicative of MS is identified. Preferably, the protocol involves oral administration of a pill or water-soluble mixture, or injection, preferably intravenous injection, of the pharmaceutical composition. In the case of rheumatoid arthritis, the pharmaceutical composition may be administered when patients exhibit clinical symptoms of the disease. In the case of insulin-induced diabetes mellitis, the pharmaceutical composition is administered when patients have clinical symptoms, or when a genetic mutation indicative of diabetes mellitus is identified. The protocol involves oral administration of the pharmaceutical composition, which preferably is in the form of a pill or water soluble mixture, or injection of the pharmaceutical composition, preferably intravenous injection.

The present invention also relates to a method of blocking activation and proliferation of CD4+T cells in vitro and in vivo.

The present invention also relates to a method of preventing T-cell mediated rejection of an allograft transplant. The method comprises administering a CD 28 peptide mimetic to a patient that has recently undergone, or is about to undergo, such transplant. Preferably, the peptide mimetic is administered to such a patient intravenously.

The CD 28 peptide mimetics are prepared using standard techniques and equipment for preparing synthetic peptides, such as a synthesizer. For example, the CD 28 peptide mimetics may be prepared using the 9600 Millegen/Biosearch synthesizer or a 40 well multiple peptide synthesizer (MPS 396, Advanced Chem Tech, Louisville, Ky.) and purified by reverse phase HPLC (Water's Associates) and characterized by electrospray ionization spectrometry (Mass Spectral facility, OSU). Retro-inverso peptides are assembled in a reverse order of amino acids with Fmoc-D-amino acid derivatives.

Pharmaceutical Composition

The pharmaceutical composition comprises a biologically effective amount of a CD 28 peptide mimetic, and preferably a relatively inert topical carrier. Many such carriers are routinely used and can be identified by reference to pharmaceutical texts.

The acceptable carrier is a physiologically acceptable diluent or adjuvant. The term physiologically acceptable means a non-toxic material that does not interfere with the effectiveness of the antagonist. The characteristics of the carrier will depend on the route of administration and particular compound or combination of compounds in the composition. Preparation of such formulations is within the level of skill in the art. The composition may further contain other agents which either enhance the activity of CD 28 mimetic or complement its activity. The composition may further comprise fillers, salts, buffers, stabilizers, solubilizers, and other materials well known in the art.

Dosage

In vivo, a biologically effective amount is an amount sufficient to sufficient to show a meaningful benefit, i.e., partially or completely relieve the symptoms associated with the respective disease or disorder. The amount of the CD 28 peptide mimetic required will depend upon the nature and severity of the condition being treated, and on the nature of prior treatments which the subject has undergone and the type of defect or disease being targeted. Ultimately, the dosage will be determined using clinical trials. Initially, the clinician will administer doses that have been derived from animal studies. An effective amount can be achieved by one administration of the composition. Alternatively, an effective amount is achieved by multiple administration of the composition to the subject. In vitro, the biologically effective amount is the amount sufficient to reduce proliferation or activation of CTLA4+ T cells.

Between 0.125 mg and 5 mg will be administered, in two-fold increments, to determine the full range of inhibition of EAE and toxicity of the CD 28 peptide mimetic. The efficacy of oral, subcutaneous and intravenous administration is determined in clinical studies.

Autoimmune Diseases

Multiple Sclerosis.

MS is a demyelinating disease of the central nervous system that likely results from a combination of genetic susceptibility, environmental factors, pro-inflammatory cytokines released in the CNS and autoimmune reactions. MS pathology consists of CNS inflammatory infiltrates containing CD4+ autoreactive T cells and demyelination. Hence, MS is considered to be an autoimmune disease of the CNS that is triggered by an unknown stimulus. A cascade of inflammatory events leads to the activation of the immune system that perpetuates the inflammatory process. T cells specific for myelin antigens arise as a primary or secondary event in MS, which damages myelin and destroys oligodendrocytes leading to demyelination. Thus a CD4+ T cell mediated immune response plays a central role in the pathogenesis of MS. Depending on the extent of demyelination and rate of remyelination, the MS disease course is variable and is classified as relapsing-remitting, primary progressive, secondary progressive and progressive relapsing.

The EAE Model:

EAE is an animal model used to design and test interventions in the MS disease process because of its clinical, immunological and histopathological similarities to MS. EAE is an experimental autoimmune disease of the CNS that results from the immunization of susceptible animals with myelin proteins, including myelin basic protein (MBP), proteolipid protein (PLP), myelin oligodendrocyte glycoprotein (MOG) or peptides derived from these proteins. EAE is mediated by activated CD4+ T cells that recognize the neuroantigen in the context of major histocompatibility complex (MHC) Class II molecules. The resulting immune response initiates a series of events including CNS mononuclear cell infiltration, demyelination, perivascular edema, and ascending paralysis. EAR in susceptible mouse strains, including B10.PL, SLJ, and PL/J is characterized by a relapsing remitting (R-EAE) disease course, in which animals undergo an initial acute episode, followed by remission, with progression to multiple relapses. R-EAE is initiated in mice by either immunization with myelin antigens combined with CFA and pertussis toxin (PT) or by adoptive transfer of activated myelin specific CD4+ T cells. The N acetylated 1-11 (NAc 1-11) peptide of MBP is the immunodominant epitope recognized by encephalitogenic CD4+ T cells in the context of MHC Class II I-A$^u$ (H-2$^u$) in the B10.PL mouse. In the immune response to this peptide in I-A$^u$ mice, there is preferential usage of the Vb8 T cell receptor (TCR) genes. This finding has led to the development of TCR transgenic mice overexpressing the MBP-specific TCR (Va4 V).

T Cell Activation and EAE:

T cell clonal expansion is initiated through the recognition of a peptide MHC complex by the T-cell receptor. Complete T cell activation requires further signaling via costimulatory molecules. Once activated, naive CD4+ (Th0) cells can develop distinct effector phenotypes depending on the local cytokine milieu and type of costimulatory molecules expressed by the antigen presenting cell (APC). IL-12 released by APC biases naive cells towards the Th1 phenotype, which is characterized by the production of IL-2 and the pro-inflammatory cytokines INF-$\lambda$ and TNF-$\alpha$. CD4+T cells of the Th1 phenotype are required for EAE induction in immunocompetent animals. Studies performed on transgenic animals with EAE have shown that expansion of T cells specific for myelin antigens is required to obtain CNS perivascular inflammatory infiltration and demyelination.

The present invention will be described in greater detail with the aid of the following examples which should be considered as illustrative and non-limiting.

EXAMPLES

Example 1

CD28 Peptide Mimetic Synthesis and Characterization

Analog Design:

CD28 is a member of a subfamily of molecules within the immunoglobulin superfamily which contains a single IgV domain. Sequence alignment of the IgV fold revealed a rigorous conservation of a hexapeptide motif "MYPPPY" in the CDR3-like region of CD28. The localization of the motif in the solvent exposed CDR3-like region and conservation across species strongly suggested the presence of a candidate ligand binding epitope in this region. The hydrophobic motif forms a loop that is conformationally constrained due to the presence of adjacent proline residues.

Based on molecular modeling of the CD28 extracellular domain, a 20 residue linear peptide was defined that comprised the conserved polyproline motif and flanking sequence such that the predicted sequence had a greater propensity to form an helical structure as predicted by the secondary structure algorithm by Chou and Fasman. The sequence of this L form of the CD 28 peptide mimetic is KIEFMYPPPYLDNERSNGIE, SEQ ID NO: 5.

In order to mimic the end groups of the ligand binding epitope of parent CD28 molecule the amino terminus of free L CD28 peptide mimetic was acetylated and the carboxy terminus was amidated. In addition, this modification neutralizes charges at the termini of the peptide. This modification stabilizes the secondary structure, and is expected to enhance the functional interaction of the molecule with B7 ligands.

Unmodified peptides can be susceptible to enzymatic degradation and rapid clearance from circulation. Accordingly, a retro-inverso isomer of the above described L CD28 peptide mimetic was designed. Retro-inverso peptides are peptides made of reversed D-amino acids, so they are mirror images of a mirror image. The use of D amino acids results in inverted chirality and the reversed order of amide bonds (—NHCO— instead of —CONH—) and creates an analogue that regenerates both the planarity of peptide bonds and the spatial orientation of side chains closely related to that of the original peptide. The retro-inverso peptide was assembled in a reverse order of amino acids with Fmoc-D-amino acid derivatives. The retro-inverso peptide, i.e., the D CD28 peptide has the sequence EIGNSRENDLYPPPYM-FIEK, SEQ ID NO: 6.

As control, all D-amino acid CD28 enantiomers, and a CD28 peptide with the amino acid sequence in the reverse order were also synthesized. The CD 28 peptide mimetics and the control peptides are summarized in Table 1 below.

(Rink amide) resin (Advanced Chemtech, Louisville, Ky.) as peptide amides. Coupling reactions utilized six equivalents of each amino acid with 1-hydroxybenzotriazole (HOBT), 2-(1H-benzotriazole-1-yl)-1,1,3,3,-tetramethyluronium tetrafluoroborate and distilled diisopropylethylaime (DIEA). Deprotection was accomplished with 30% piperidine in DMF. Immediately after the final deprotection step, the free $NH_2$ group of the terminal amino acid residue was acetylated with 5 ml of 3 mmol acetaimidazole in DMF (50 ml). The completion of acetylation was confirmed by a negative Kaiser Ninhydrin test. With respect to the parent peptide, the retro-inverso peptide was assembled in reverse order of amino acids with Fmoc-D-amino acid derivatives. The peptides were cleaved from the resin support with simultaneous side-chain deprotection by acidolysis using TFA with 5% phenol, 5% thioanisole and 2.5% ethanedithiol as scavengers. The crude peptides were purified by semi-preparative reverse phase high performance liquid chromatography (RP-HPLC) using a $C_{18}$ column (10 mm by 25 cm) (Vydac, Hesperia, Calif.) at a temperature of 32.5° C. and a flow rate of 5 ml/min. Peptides (5–10 mg per run) were loaded in 0.1 M acetic acid and chromatographed for 30 mm with a linear gradient of 10–60% of acetonitrile in water containing 0.1% trifluoroacetic acid (TFA). The separations were monitored at 230 and 280 nm.

Analytical HPLC was run using a VIDAC $C_{18}$ column (4.6 mm by 25 cm) using the same gradient as stated above. Eluants were monitored at 214 and 254 nm. Purified peptides were obtained in greater than 95% purity as assessed by reverse-phase HPLC. The identity of peptides was finally confirmed by matrix-assisted laser desorption/ionization time of flight mass spectrometry.

A. Structural Characterization of the Synthetic CD28 Peptide Mimetics and Control Peptides Circular dichroism (CD) spectroscopy is sensitive to the secondary structure of globular proteins. CD spectroscopy is a useful tool for determining whether a polypeptide or protein adopts a polyproline (PP) II type helical conformation in solution.

To determine the nature of the secondary structure of the peptides shown in Table I, CD spectra of CD28 peptide mimetics, as well as the control peptides, were recorded at

TABLE 1

Amino acid sequences of CD28 peptide mimetics and control peptides

| CD28 Peptide Sequence | Abbreviation | Identity |
|---|---|---|
| $NH_2$KIEFMYPPPYLDNERSNGTICOOH | L-CD28 | Free L peptide |
| $CH_3COL[KIEFMYPPPYLDNERSNGTI]LCONH_2$ | EL-CD28 | End-blocked L-peptide |
| $CH_3COD[ITGNSRENDLYPPPYMFEIK]DCONH_2$ | RI CD28 | Retro-inverso D-peptide |
| $CH_3COD[KIEFMYPPPYLDNERSNGTI]DCONH_2$ | D-CD28 | D-peptide (Control) |
| $CH_3COL[ITGNSRENDLYPPPYMFEIK]LCONH_2$ | RL-CD28 | Reverse-L-peptide (Control) |

Peptide Synthesis and Purification:

The CD 28 peptide mimetics and control peptides shown in Table 1 above were synthesized by solid phase peptide synthesis following Fmoc/DCC/HOBt methodology on a fully automated peptide synthesizer (Model 396-5000 Multiple Peptide Synthesizer, Advanced Chemtech, Louisville, Ky.). The free L CD28 peptide was assembled on 4-methylbenzhydrylamine resin (0.5 mmol/g substitution) with 4-(hydroxymethyl) phenoxyacetic acid as the linker. The end group blocked peptides were assembled on Fmoc-2,4-dimethyloxy-4'-(carboxymethyloxy)-benzylhydrylamine 25° C. Circular dichroism measurements were recorded at room temperature on an AVIV Model 62A DS spectrometer equipped with a thermostatic temperature controller and microcomputer as described previously Lairmore, M. D., A. M. DiGeorge, S. F. Conrad, A. V. Trevino, R. B. Lal, and P. T. Kaumaya. 1995. Human T-lymphotropic virus type 1 peptides in chimeric and multivalent constructs with promiscuous T-cell epitopes enhance immunogenicity and overcome genetic restriction. *J Virol* 69:6077). CD spectra were recorded in a quartz cell of 0.1 cm pathlength. Each spectrum was obtained by averaging one nm/sec in the 190 to 270 nm wavelength range, using a bandwidth of 1.0 nm and a response time of 1 s.

CD28 peptides were dissolved in PBS, pH7.4, in 50% trifluoroethanol (TFE) or in 4 M –6 M CaCl$_2$ at 412 µM concentration for CD measurements. The CD spectra were recorded at a range of temperatures between 5° C. and 90° C. Raw CD signals (in millidegrees) were converted to mean residue ellipticity (MRW) in deg.cm$^2$/dmol using the formula $[\theta]_{MRW}=[\theta]_{obs}/101$ cn where $\theta_{obs}$ is the observed ellipticity, 1 is the path-length in cm, c is the molar concentration of peptide and N is the number of residues in the peptide.

Figure 1A:
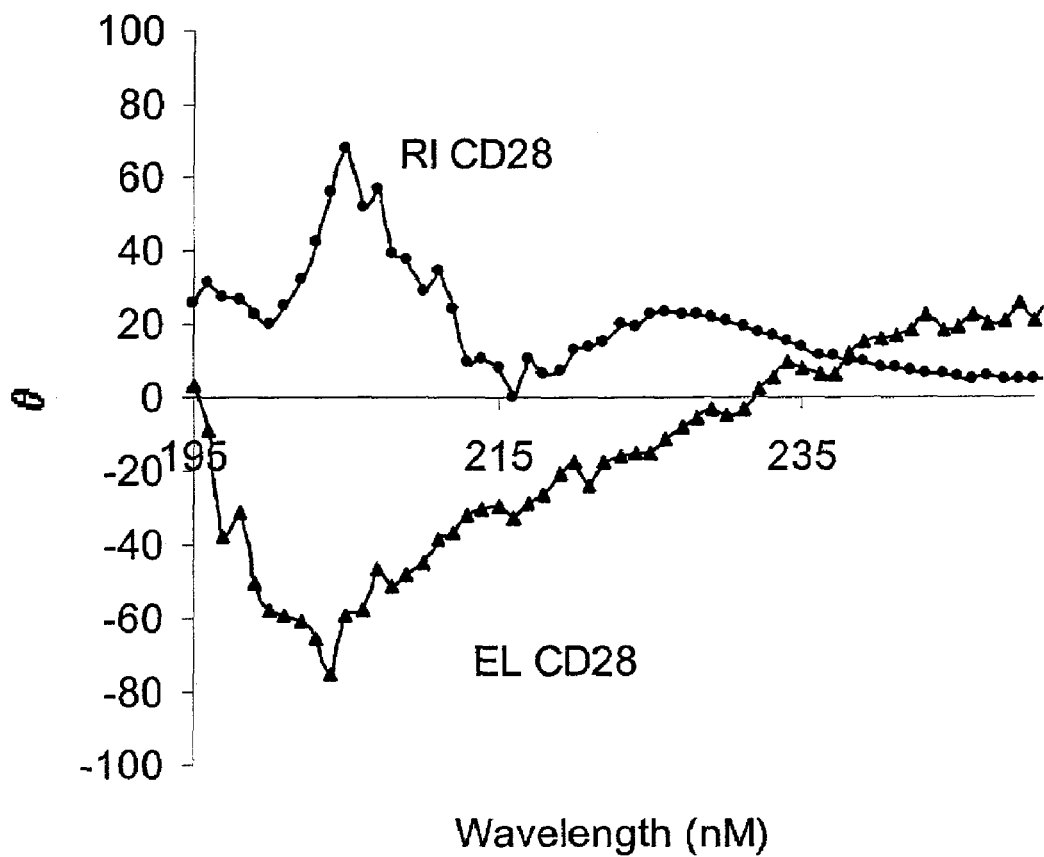
Figure 1B:
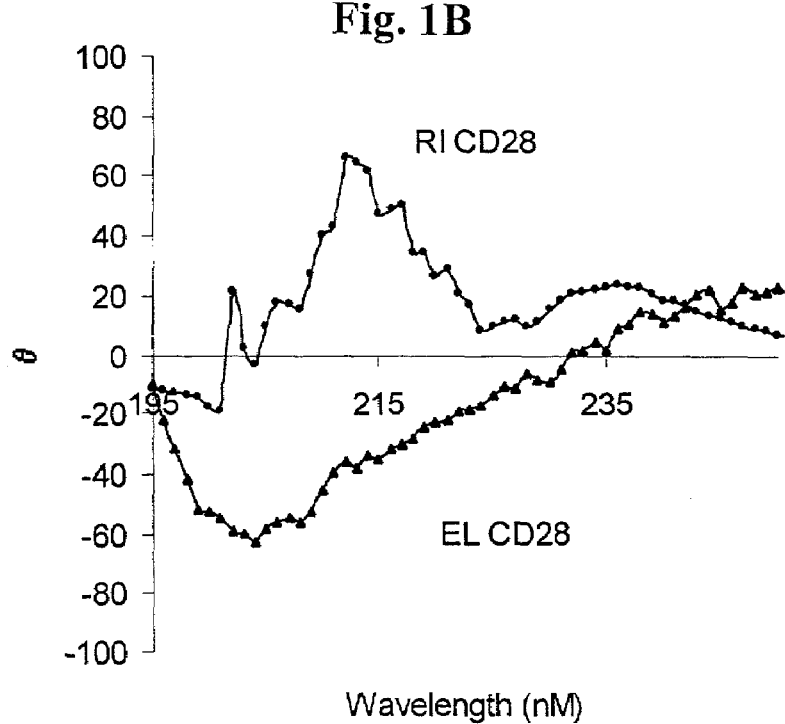

The CD spectrum of free L CD28 peptide mimetic showed a large minimum at 202 nm ($\theta=-62.73\times10^3$ deg.cm$^2$.dmol$^{-1}$) and a slight maximum at 221 nm ($\theta=-3.5\times10^3$ deg. cm$^2$dmol$^{-1}$)(data not shown) at 25° C. The CD spectrum of EL CD28 peptide mimetic presented a strong mean residue molar ellipticity minimum at 205 nm ($\theta=-69\times10^3$ deg.cm$^2$.dmol$^{-1}$) and a weak maximum at 221 nm ($\theta=-17\times10$ deg. cm$^2$.dmol$^{-1}$) although still in the negative ellipticity region at 25° C. Compared to the free L CD28 spectrum, the intensity of ellipticity near 200 nm was considerably enhanced in the EL CD28 peptide mimetic, suggesting stabilization of the helical secondary structure (data not shown). When the temperature was raised to 90° C., the mean residue molar ellipticity was decreased ($\theta=-62.32\times10^3$ deg. cm$^2$.dmol$^{-1}$)(FIG. 1B). Similar variation with increasing temperature has been observed in proline-rich peptides, due to a transition from the PP II helical structure to a disordered random coil conformation (Antonyraj, K. J., T. Karunakaran, and P. A. Raj. 1998. Bactericidal activity and poly-L-proline II conformation of the tandem repeat sequence of human salivary mucin glycoprotein (MG2). *Arch Biochem Biophys* 356:197). When the CD spectrum of EL CD28 peptide dissolved in 6 M Ca Cl$_2$ was recorded at 25° C., the intensity of mean residue ellipticity minimum at 205 nM was drastically decreased ($\theta=-28\times10^3$ deg. cm$^2$.dmol$^{-1}$) suggesting complete disruption of the helical structure (FIG. 1A). These observations are consistent with the CD spectrum of polypeptide sequences reported to prefer a PP II type helical structure. (Sreerama, N., and R. W. Woody. 1994. Poly(pro)II helices in globular proteins: identification and circular dichroic analysis [published erratum appears in Biochemistry 30 May 1995;34 (21):7288]. *Biochemistry* 33:10022.)

The CD spectrum of the RI CD28 peptide mimetic at 25° C. presented a mean residue ellipticity maximum at 205 nm ($\theta=57\times10^3$ deg. cm$^2$. dmol$^{-1}$), a weak minimum at 215 nm ($\theta=1.14\times10^4$ deg. cm$^2$.dmol$^{-1}$) and a weak maximum at 223 nm ($\theta=18.3\times10^3$ deg. cm$^2$.dmol$^{-1}$) (FIG. 1A). Similar mirror-image like CD spectra of retro-inverso isomers of L peptides have been previously reported (Petit, M. C., N. Benkirane, G. Guichard, A. P. Du, M. Marraud, M. T. Cung, J. P. Briand, and S. Muller. 1999. Solution structure of a retro-inverso peptide analogue mimicking the foot-and-mouth disease virus major antigenic site. Structural basis for its antigenic cross-reactivity with the parent peptide. *J Biol Chem* 274:3686.) By increasing the temperature to 90° C., the molar ellipticity maximum markedly decreased in intensity ($\theta=17.2.9\times0^3$ deg. cm$^2$ dmol$^{-1}$) and shifted to a longer wavelength (211 nM). The CD spectrum of the retro-inverso CD28 peptide mimetic dissolved in 6 M CaCl$_2$ showed a dramatic decrease in molar ellipticity maximum at 205 nM ($\theta=1.10\times10^4$ deg. cm$^2$.dmol$^{-1}$), complete loss of molar ellipticity minimum at 215 nM and the maximum at 223 nM (FIG. 1B). These observations reflect the destabilizing effect of CaCl$_2$ on the PPII helical conformation adopted by the retro-inverso CD28 peptide mimetic.

The CD spectrum of a six residue free peptide comprising the "MYPPPY" (SEQ ID NO: 1) motif alone showed a weak minimum ($\theta=-8.6\times10^1$ deg. cm$^2$ dmol$^{-1}$) at 208 nm (data not shown). This suggests that the length of the CD28 peptide and the side chain interactions with the flanking residues play a role in the formation of a PP II helix.

B. Interaction of the CD 28 Peptide Mimetics with B7-1

Binding experiments were performed by surface plasmon resonance (SPR) on an instrument sold under the trademark BIACORE™ from Pharmacia Biosensor (Uppasala, Sweden). All experiments were performed at 37° C. using HBS-EP buffer (25 mM Hepes, pH7.4, 150 nM NaCl, 3.4 mM EDTA and, 005% surfactant P20) supplied by Pharmacia Biosensor.

CD80-Ig (extracellular domain of CD80 fused with the constant region of mouse IgG1 heavy chain) at 35 µg/ml in 10 mM sodium acetate buffer, pH 4.2, was coupled to a research grade CM 5 sensor chip using a standard amine coupling procedure with the following modifications (38). To reduce the immobilization level of the ligand, the surface was activated for 3 (instead of 7) minutes with N-hydroxysuccinamide and N-hydroxymethyl-N-(3-diethylaminopropyl) carbodiimide. This typically resulted in immobilization of 1422–1660 RU of CD80-Ig on the sensor chip. Following coupling, noncovalently bound ligand was removed by washing twice with 5 mM NaOH.

Kinetic analysis was performed by injecting the analytes (L-CD28, EL-CD28, RI CD 28, RL CD28 and D CD28 peptides) at 0.375 µM to 18.5 µM concentrations in HBSS-EP, pH7.4, for 300 s with a flow rate of 10 µl/min. The analytes were also injected at the same concentration and injection times over an empty flow cell with nothing immobilized.

Competitive Kinetic Analysis.

Competitive kinetic analysis was performed as described previously using purified anti-mouse IgG1 Fc (31437zz) (Pierce City, Ill., USA) to indirectly immobilize CD80-Ig (39). This resulted in 286–342 RU of CD80-Ig bound to the chip. The binding kinetics of CD28-Ig was assessed by injecting a range of CD28-Ig concentration (187 nM to 12 µM) over immobilized CD80-Ig (324 RU) for 5 min at 10 µl/min. CD80-Ig was regenerated using a 3 min injection of 5 mM NaOH. For competitive kinetic analysis, 100 µl of a 3.2 µM CD28-Ig solution was mixed with 100 µl of EL CD28 or RI CD28 peptides (6.18 µM to 503 µM in HBS-EP) and injected over the surface of CD80-Ig as secondary analyte for 5 min with a flow rate of 10 µl/min. The CD80-Ig surface was regenerated between injections by washing for 3 min with 5 mM NaOH. The mixtures were also injected on an empty flow cell with no protein immobilized, as a control.

Data analysis was performed with BIAEVALUATION™ software version 2.1(Pharmacia Biosensor AB). The binding as measured in response units (RU) in BIACORE™ and the binding rate, dR/dt, can be used to evaluate the kinetics of the synthetic CD28 peptides—CD80-Ig interaction. Prior to kinetic analysis, data were adjusted to zero baseline level by subtracting the background responses obtained by injection of the analytes through a control flow cell with no ligand immobilized. Data from direct kinetic analysis were analyzed as follows. First, the dissociation rate constant, $k_d$, (units: s$^{-1}$) was determined, by fitting experimental data from the buffer flow part of the sensogram to the equation $$R(t)=R_1 * e^{-kd*(t_0-t_1)} \qquad (1)$$

where $t_0$ is the injection time, $R_1$ is the response level at the start of dissociation time $t_1$ and $k_d$ is the dissociation rate constant.

The $k_d$ value obtained was used as a constant during the analysis of the injection phase data. Binding data above the noise level was selected by converting the sensogram to a plot of the logarithm of the binding rate vs time (dR/dt vs. time). The $k_a$ was determined by nonlinear curve fitting of the following equation $$R(t)=R_{eq}*\{1-e^{-(k_a*C+k_d)*(t)}\} \quad (2)$$

where R(t) is the response at time t, $R_{eq}$ is the steady state response level, $k_a$ is the association rate constant (units: $M^{-1}s^{-1}$), $k_d$ is the dissociation rate constant and C is the concentration of the injected peptide analyte. An offset was added to account for the refractive index differences between the analyte and the running buffer.

In competitive kinetic experiments, the observed response R is the sum of the contributions of $R_1$ and $R_2$ from the two analytes. The binding data was analyzed using the equation $$R(t)=R_{1\ (CD28\text{-}Ig)}+R_{2\ (CD28\text{-}P)} \quad (3)$$

where $R_1=R_{max}k_{a1}C_1/k_f-k_s\{k_1(k_f-k_s)/k_f*k_s+k_1-k_f/k_f*e^{-k_f(t-t0)}-k_1k_s/k_s*e^{-ks(t-t0)}\}$ $R_2=R_{max}MW_1k_{a2}C_2/MW_2*k_f-k_s[\{k_2(k_f-k_s)\}/k_f*k_s\}+(k_2-k_f/k_f)*e^{-k_f(t-t0)}-(k_2-k_s/k_s)*e^{-ks(t-t0)}$ $k_f=0.5\{k_{tq}+k_2+\pi(k_{a1}-k_2)^2+4kf_1k_{CD28P}C_1C_2\}$ $k_s=0.5\{k_{t1}+k_2-\pi(k_{t1}-k_2)^2+4k_1k_2C_1C_2\}$ $k_{t\ CD28\text{-}Ig}=k_{a1}C+k_{d1}$ $k_{t2}=k_{a2}C_2+k_{d2}$ When competitive data were analyzed, $k_a$, $k_d$ and $R_{max}$ values obtained for the interaction between CD80-Ig and CD28-Ig were used as non floating parameters and the rate constants for CD28 peptides were calculated from the injection phase data using the expanded equation 3.

After analyzing sensograms obtained from injections of increasing concentrations of peptide analytes or CD28-Ig, the experimental data was analyzed using the BIAsimulation software 2.1. A plot of the logarithm of (dR/dt) against time was calculated from the sensograms, and then the slopes at different concentrations were plotted against the concentrations of the peptide analyte. Different angles obtained of the linear lines represent the variation of affinities, which gives the association rate constant ($k_a$) from the equation $$\ln dR/dt = \ln(k_a CR\ max) - K_a C + k_d)t \quad (4)$$

where dR/dt is the rate of change of the SPR signal, C is the concentration of the analyte, $R_{max}$ is the maximum analyte binding capacity in RU and R is the SPR signal in RU at time t. The dissociation rate constant is obtained from the equation $$K_d = k_d/k_a \quad (5)$$

Figure 3A:
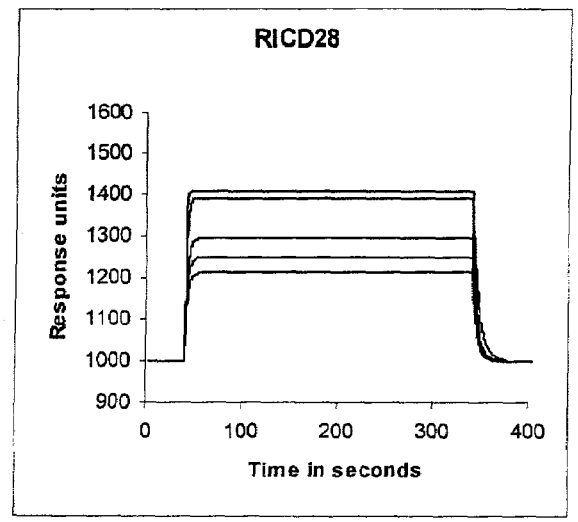
Figure 3B:
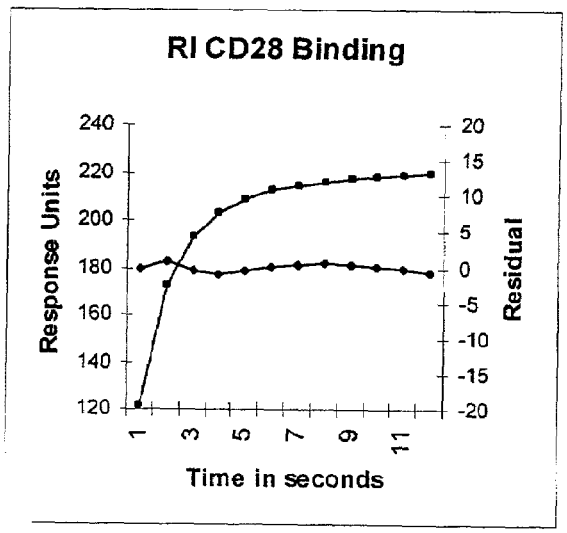
Figure 3C:
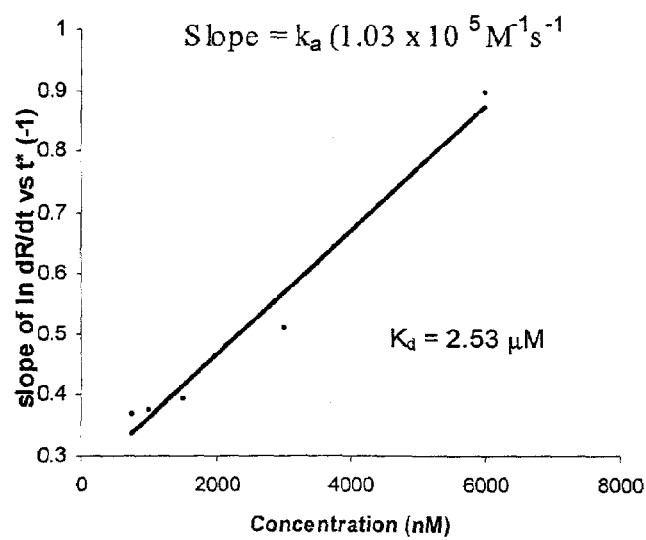

Sensograms from direct kinetic analyses of EL CD28 and RI CD28 peptides mimetics at different concentrations from one experiment are represented in FIGS. 2 and 3 respectively. Both peptides reached equilibrium binding very rapidly (12–20 s) and in the washing phase dissociated rapidly (10–12 s). Similar features of fast binding kinetics have been reported for the B7:CD28 interaction (33, 48). The background responses following injection of EL CD28 and RI CD28 peptide mimetics over an empty flow cell with no protein immobilized are equivalent and very similar to the responses obtained following injections of control peptides (data not shown). The maximum response units obtained for binding to CD80-Ig was 478 RU, 667.5 RU and 444.2 RU for L CD28, EL CD28 and RI CD28 peptide mimetics respectively. The response units observed at the beginning and end of the experiments were similar indicating that the bound CD80-Ig was stable. Dissociation of L CD28, EL CD28, and RI CD28 peptides from bound CD80-Ig was analyzed from the buffer flow phase of the sensogram and the dissociation rate constant ($k_d$) for each curve was determined using equation (1). The injection phase of the sensogram was analyzed using equation (2) by nonlinear curve fitting incorporating the calculated $k_d$ value to obtain the $k_a$ value for each curve. The calculated parameter values with standard error are presented in Table 2.

Data for both $k_a$ and $k_d$ are quite consistent over the entire range of concentrations used. The difference between experimental and calculated data for both EL CD28 and RI CD28 peptide mimetics estimated by $Chi^2$ value is low being close to the noise level of the instrument. A linear regression plot of the rate of change in the response against response units was plotted using these values of $k_a$ and $k_d$ for each CD28 peptide analyte. The slope of this plot was then plotted against the concentration of the peptide to yield a $k_d$ of 2.44 μM, 2.34 μM and 2.53 μM for L CD28, EL CD28 and RI CD28 peptide mimetics, respectively, for binding to CD80-Ig. Consistent with the lack of PP II helix formation as observed by CD studies, a synthetic consisting of the hexapeptide motif alone did not bind CD80-Ig (data not shown).

TABLE 2

| APR | C (nM) | $k_a$ | SE $k_a$ | $Chi^2$ | $k_d$ | SE $k_d$ | $Chi^2$ |
|---|---|---|---|---|---|---|---|
| EL CD28 | 6.00E+03 | 1.11E+05 | 7.96E+03 | 4.07E−01 | 2.73E−01 | 2.52E−02 | 1.22E+00 |
|  | 3.00E+03 | 1.37E+05 | 1.10E+04 | 7.02E−01 | 0.214 | 0.0283 | 9.05E−01 |
|  | 1.50E+03 | 1.15E+05 | 9.33E+03 | 2.20E−02 | 2.42E−01 | 9.33E−02 | 1.02E+00 |
|  | 7.50E+02 | 1.10E+05 | 1.23E+04 | 2.92E−02 | 2.74E−01 | 5.00E−02 | 1.23E+00 |
|  | 3.75E+02 | 2.46E+05 | 5.63E+04 | 2.04E−01 | 3.99E−01 | 2.49E−02 | 1.31E+00 |
| RI CD28 | 6.00E+03 | 1.12E+05 | 9.05E+03 | 4.74E−04 | 2.28E−01 | 3.47E−02 | 6.75E−02 |
|  | 3.00E+03 | 1.22E+05 | 2.31E+04 | 3.96E−03 | 1.46E−01 | 1.67E−02 | 1.26E−02 |
|  | 1.50E+03 | 1.41E+05 | 5.14E+04 | 1.00E−01 | 1.83E−01 | 2.79E−02 | 7.12E−02 |
|  | 1.00E+03 | 1.71E+05 | 5.77E+04 | 1.12E−02 | 2.05E−01 | 3.09E−02 | 4.41E−02 |

Figure 4A:
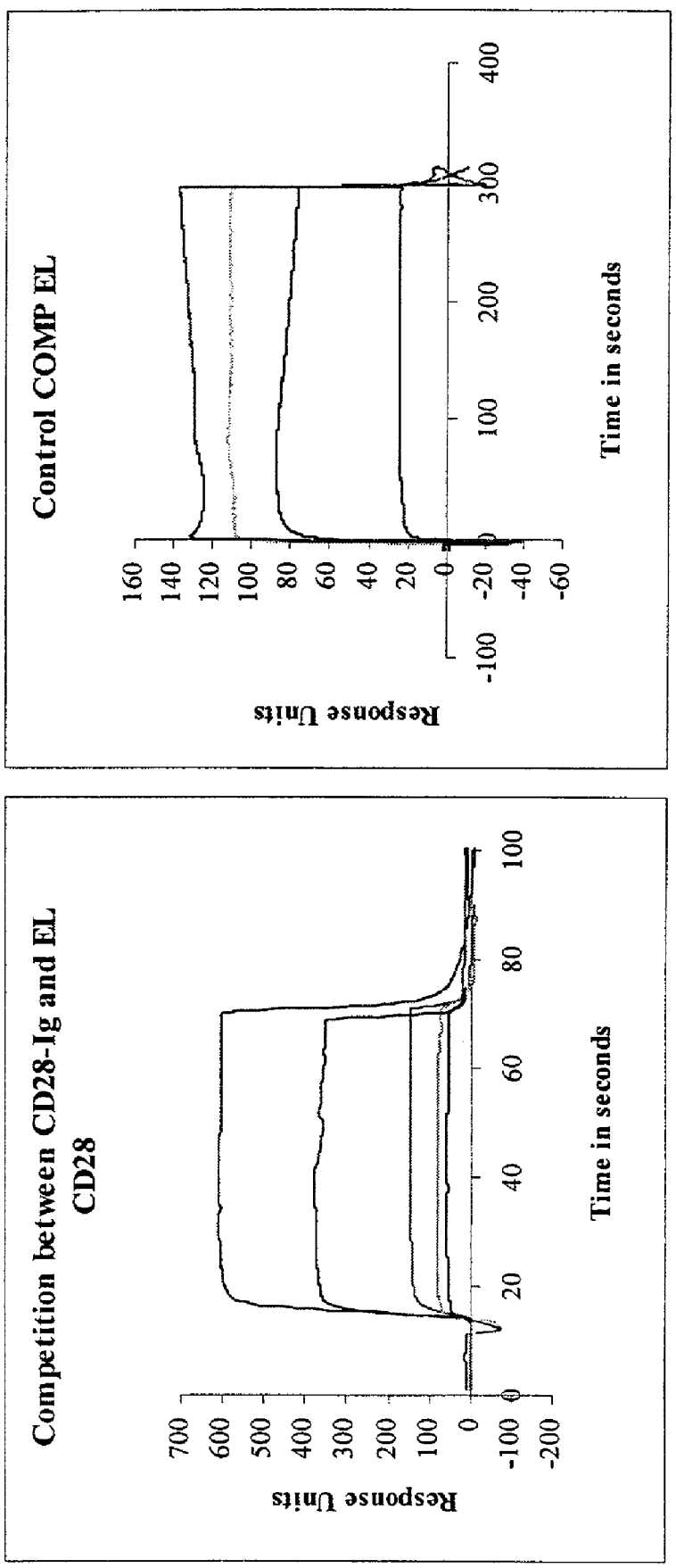
Figure 4B:
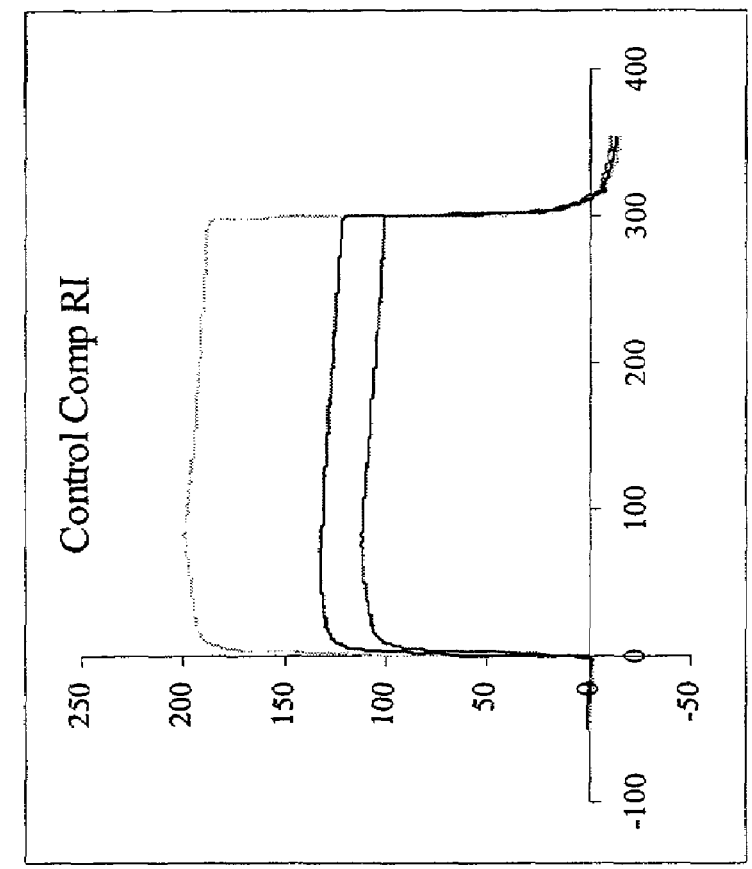
Figure 4B:
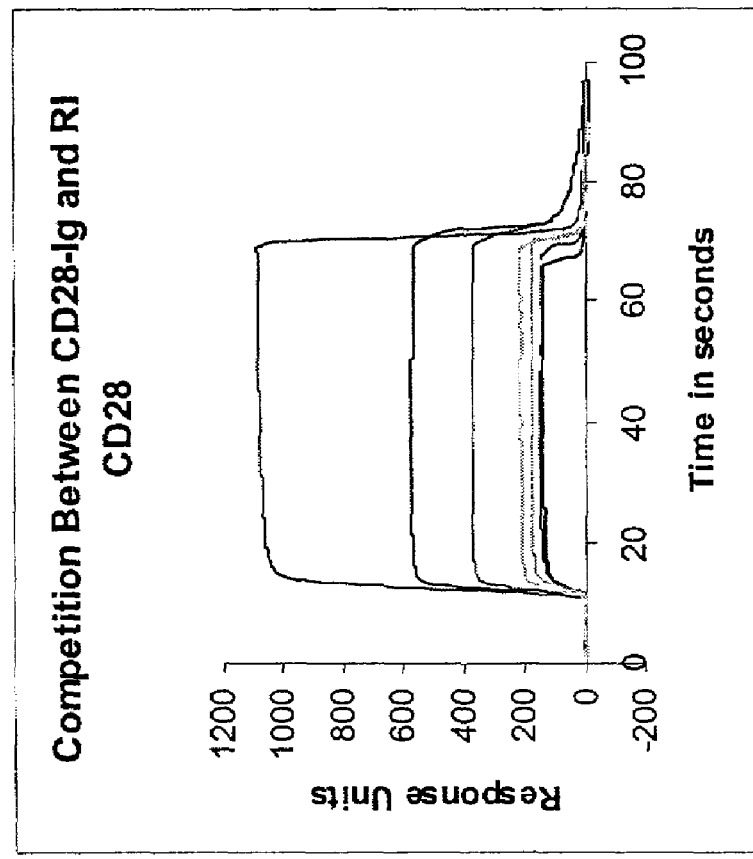
Figure 4C:
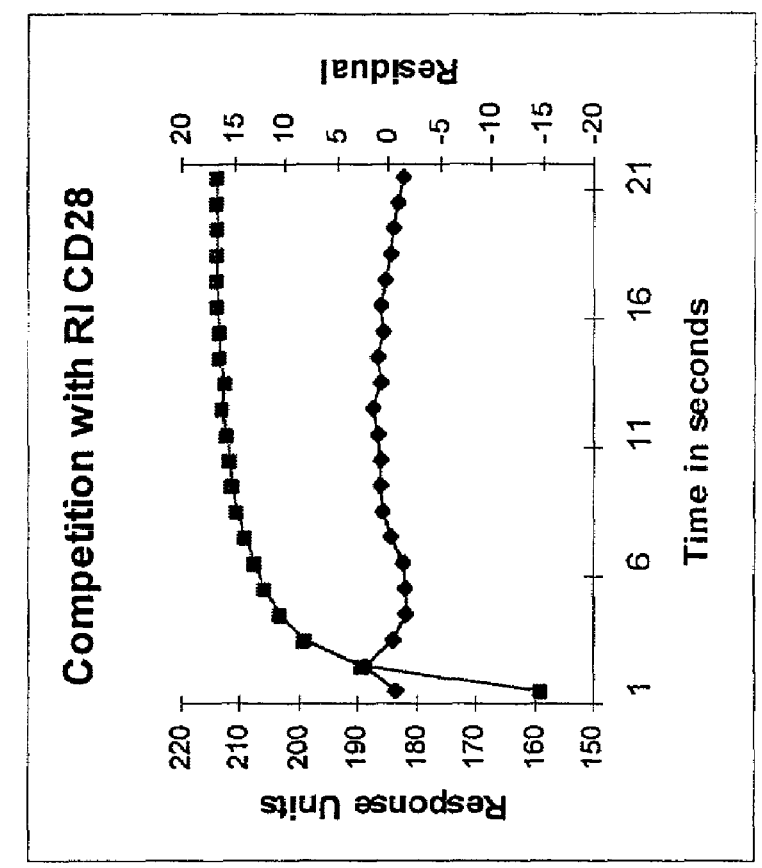
Figure 4C:
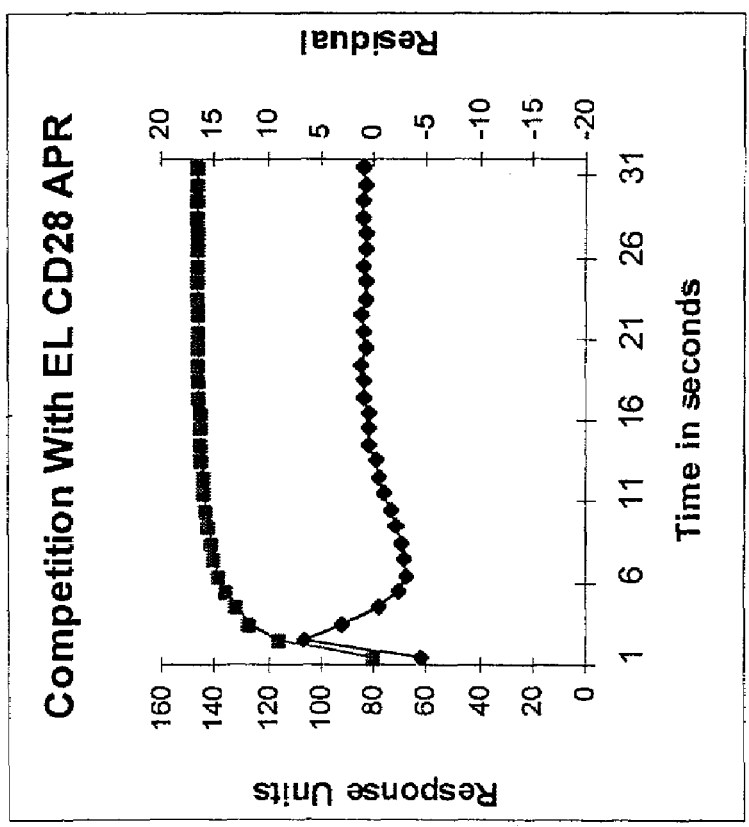

In the method used for competitive kinetic analysis, indirect immobilization resulted in 286–342RU of CD80-Ig bound via anti mouse IgG1Fc mAB coupled to the sensor chip surface. FIGS. 4a and 4b are representative sensograms obtained from the competitive experiments using the CD28-Ig and ELCD28 and RICD28 APR respectively. The top curve is the interaction of CD28-Ig (3.2 μM) alone with the CD80-Ig. The response level gradually goes down as the concentration of the specified CD28 peptide increases. The values obtained from the kinetic analysis for the interaction of CD28-Ig (MW=50,264.36 Da, $k_a=1.38 \times 10^5$ $M^{-1}s^{-1}$, $k_d=0.563$ $s^{-1}$) were used as invariant parameters in competitive kinetic analysis with EL CD28 and RI CD28 (MW=2425.25 Da) peptides and values for the association and dissociation rate for competing CD28 peptide analytes were floated while fitting the injection phase of the curves to the expanded equation (3). The calculated parameter values are given in Table 3. The average dissociation constant for EL CD28 peptide mimetic binding to CD80-Ig ($K_d$=2.79 μM +/−1.32) compares well with the value obtained with direct binding of the peptide to CD80-Ig ($K_d$=2.34 μM). However, the dissociation constant varied with varying concentration of EL CD28 peptide mimetic(Table 3).

The average value of dissociation constant for RI CD28 peptide mimetic binding to CD80-Ig ($k_d$=1.75 μM=/−0.67) is a little lower than the value obtained with direct tion) followed by positive selection using magnetic selection columns. Purity of the CD4+ cells was greater than 90% as assessed by staining with FITC labeled anti-mouseVβ8.2 mAb (Pharmingen). During the selection process, T cells maintain a naïve phenotype with no evidence for T cell activation as measured by proliferation in culture. Purified CD4+ T-cells ($5 \times 10^4$ cells/well) were cultured together with wild type splenocytes from B10.PL mice as APC's ($10^5$ cells/well) in RPMI 1640 containing 10% FCS, 25 mM HEPES, 2 mM L-glutamine, 50 U/ml penicillin, 50 μg/ml streptomycin, and $5 \times 10-5$ M 2-ME in round-bottom 96-well plates and MBP (40 μg/ml) or MBP NAc1-11 (10 μg/ml) or media only in the presence or absence of synthetic CD28 peptide analogues at different concentrations in triplicate wells for 72 h, including a final 18-h pulse with [$^3$H] thymidine. Cultures were harvested onto glass-fiber mats using a Skatron harvester (Skatron, Sterling, Va.) and were

TABLE 3

| APR | C (nM) | $k_a$ | SE $k_a$ | $k_d$ | SE $k_d$ | Chi$^2$. | $K_d$ (μM) |
|---|---|---|---|---|---|---|---|
| EL CD28 | $3 \times 10^5$ | $2.36 \times 10^6$ | $9.29 \times 10^5$ | 6.89 | 2.66 | 1.35 | 2.92 |
| | $2 \times 10^5$ | $5.51 \times 10^4$ | $1.68 \times 10^3$ | 8.62E−02 | 2.78E−02 | 0.125 | 1.56 |
| | $1 \times 10^5$ | $3.16 \times 10^4$ | $2.38 \times 10^3$ | 8.03E−02 | 1.15E−02 | 0.841 | 2.54 |
| | $0.5 \times 10^5$ | $6.32 \times 10^4$ | $5.3 \times 10^3$ | 3.16E−01 | 2.31E−02 | 1.24 | 5 |
| | $0.25 \times 10^5$ | $3.36 \times 10^3$ | $4.3 \times 10^3$ | 1.95E−02 | 5.65E−02 | 0.0947 | 3.36 |
| | $0.125 \times 10^5$ | $7.34 \times 10^4$ | $4.61 \times 10^3$ | 1.01E−01 | 2.55E−02 | 1.89E+00 | 1.38 |
| RI CD28 | Concentrat | $k_a$ | SE $k_a$ | $k_d$ | SE $k_d$ | Chi$^2$. | $K_d$ (μM) |
| | $3 \times 10^5$ | 1.07E+04 | 8.30E+02 | 0.0206 | 0.0144 | 1.61 | 1.93 |
| | $2 \times 10^5$ | 2.35E+04 | 1.76E+03 | 0.0245 | 0.0252 | 1.41 | 1.04 |
| | $1 \times 10^5$ | 9.47E+04 | 5.72E+02 | 0.142 | 0.0112 | 0.359 | 1.5 |
| | $0.5 \times 10^5$ | 9.24E+04 | 2.32E+03 | 0.275 | 0.0252 | 0.0578 | 2.98 |
| | $0.25 \times 10^5$ | 5.44E+04 | 3.38E+03 | 0.0738 | 0.0114 | 0.685 | 1.36 |
| | $0.125 \times 10^5$ | 1.05E+05 | 8.17E+03 | 0.177 | 0.0271 | 0.53 | 1.69 | binding of the peptide to CD80-Ig ($K_d$=2.53 μM). The values of dissociation constant obtained with varying concentrations of RI CD28 peptide mimetics were more consistent (Table 3).

Synthetic CD28 peptides competed efficiently with CD28-Ig to bind B7-1. These results demonstrate that CD28 peptides form complexes with B7-1 and represent a ligand binding epitope.

Example 2

Inhibition of T cell Proliferation and Activation Using the Peptides of Example 1

The in vitro effect of varying concentration of the CD 28 peptide mimetics on CD4+ lymph node cells and spleen cells from transgenic mice bearing the Vα 4 Vβ8.2 TCR specific for MBP Ac 1-11 was determined.

Antigens: MBP was extracted from guinea pig (GP) spinal cords (Harlan Sprague Dawley, Indianapolis, Ind.). MBP NAc1-11 peptide was synthesized.

Proliferation Analysis:

CD4+ T cells were purified from pooled peripheral lymph nodes (inguinal, axillary, brachial, cervical, popliteal), and mesenteric lymph nodes and spleen of 6–8 wk old Vα4/Vβ8.2 TCR transgenic mice by positive selection. Single cell suspensions were prepared by lympholyte M gradient, washed, counted and incubated with magnetic bead conjugated anti-mouse CD4 (L3T4) (Miltenyi Biotech Corporacounted by liquid scintillation on LKB Betaplate (LKB, Rockville, Md.). The means of the triplicate were determined and the results are expressed as delta cpm (mean counts per minute of cultures with Ag-mean counts per minute of cultures with medium alone)±SD.

FIG. 5 shows a significant decrease in the proliferative responses of CD4+ LNC and spleen cells to MBP Ac1-11 when treated with EL CD28 or RI CD28 peptide mimetics, and the effect is not dose dependent. Maximum inhibition was observed in CD4+ LNC at 120 μM concentrations of L CD28 (59.5%) followed by EL CD28 (47.6%) and RICD28 (45.7%) peptide mimetics. The proliferative responses of CD4+ splenocytes were also decreased but to a lesser extent with the observed maximum inhibition of 50.2%, 38.2% and 42% with L CD28, EL CD28 and RI CD28 peptide mimetics respectively. A similar decrease in the proliferative responses to MBP was also observed (data not shown).

The control RL CD28 and D CD28 peptides did not show inhibition. The hexapeptide consisting of the hydrophobic motif only did not show inhibition of T cell-proliferation. The hexapeptide consisting of the hydrophobic motif only did not show inhibition of T cell-proliferation. These results demonstrate that treatment with synthetic CD 28 peptide effectively blocked the expansion of encephalitogenic T cells in vitro suggesting the feasibility of a therapeutic application for these peptides in vivo.

Augmentation of T cell proliferation following CD28 ligation is a result of its ability to increase the synthesis of IL-2. To determine whether the observed reduction in proliferation is reflected in the IL-2 secretion, the ELISPOT assay was performed.

Ninety-six well unifilter plates (Polyfiltronics, Rockland, Md.) were coated overnight at 4° C. with rat anti-mouse IL-2 (Clone JES6-1A12) (Pharmingen, Calif.) at 4 μg/ml. The plates were then washed 4× with sterile PBS and blocked with 1% BSA in DMEM for 2 h at room temperature. Subsequently, isolated single cell suspensions of CD4+ LNC ($5 \times 10^6$ cells/ml) and splenocytes ($10 \times 10^6$ cells/ml) were added with the antigens and CD28 peptides under the conditions as specified for the proliferation assays. After 24 h of culture in the incubator, the cells were removed by washing 3× with PBS and 4× with PBS containing Tween (1:2000) (PBST). Then biotinylated anti mouse-IL-2 (Clone JES6-5H4) (Pharmingen, Calif.) 2 μg/ml was added and incubated at 4° C. overnight. After washing 3× with PBST and 3× with PBS, goat anti-biotin antibody conjugated to alkaline phosphatase (Vector Laboratories Inc, Burlingame, Calif.) diluted to 1:1000 in PBST containing 1% BSA was added and incubated for 2 h at room temperature. The spots were visualized by adding BCIP/NBT phosphatase substrate (Kirkeguard & Perry Laboratories, Gaithersburg, Md.). Image analysis of ELISA spot assays was performed on a Series 1 Immunospot Image Analyzer (Autoimmun Diagnostika (US) Inc.) customized for analyzing ELISA spots to meet objective criteria for size, chromatic density, shape and color.

FIG. 6 shows that MBP stimulated CD4+ LNC bearing Vα4 Vβ8.2 TCR exhibited significantly reduced frequency of IL-2 secreting cells in the presence of 50 mM EL CD28 or RI CD28 peptide mimetics when compared to untreated cells. There was an increase in the frequency of IL-2 secreting antigen stimulated CD4+ LNC when higher concentrations of CD28 peptides were used. This observation perhaps reflects induction of apoptosis, since IL-2 is also known to sensitize activated T cells to cell death (50).

To investigate whether the observed decrease in proliferative responses following treatment with CD28 peptides is a result of cell loss, cell death was measured by enzymatic in-situ labeling. Apoptotic cells among MBP NAc1-11 stimulated TCR Vβ 8.2+ CD4+ T cells were detected by staining with FITC labeled Tdt (terminal deoxynucleotidyl transferase). Cells incubated in DNAse served as positive control.

CD4+ T cells from pooled lymph nodes and spleen from B10.PL TCR Vβ 8.2 Vα 4 transgenic mice were cultured in RPMI 1640 in a 96 well round-bottom plate, essentially under the conditions specified for proliferation assays. Cells were harvested at the end of 48 hours and apoptotic cells among TCR Vβ 8.2+ CD4+ T cells were detected by the TUNEL method. Briefly, after washing twice with PBS containing 1-% rat serum, the cells were stained with PE labeled anti-mouseVβ 8.1,8.2 TCR (clone MR5-2) (Pharmingen, San Diego, Calif.) for 30 min at room temperature and washed. Subsequently, the cells were fixed with 4% paraformaldehyde in PBS for 30 min at room temperature. Then the cells were washed and permeabilized with 0.1% Triton X-100 in 0.1% sodium citrate for 2 min at 4° C. After washing, the DNA strand breaks in the cells were detected by incubating the cells with fluorescein labeled TUNEL mix (terminal deoxynucleotidyl transferase (Tdt)) for 60 min at 37° C. using an in situ cell death detection kit (Boehringer Mannheim, Mannheim, Germany) according to the manufacturer's recommendations. As a positive control, cells were incubated in DNAse (1 mg/ml) for 10 minutes at room temperature prior to incubation with TdT. The negative control consisted of cells incubated without TdT. Cells were then washed with PBS and analyzed by flow cytometry.

Figure 7A:
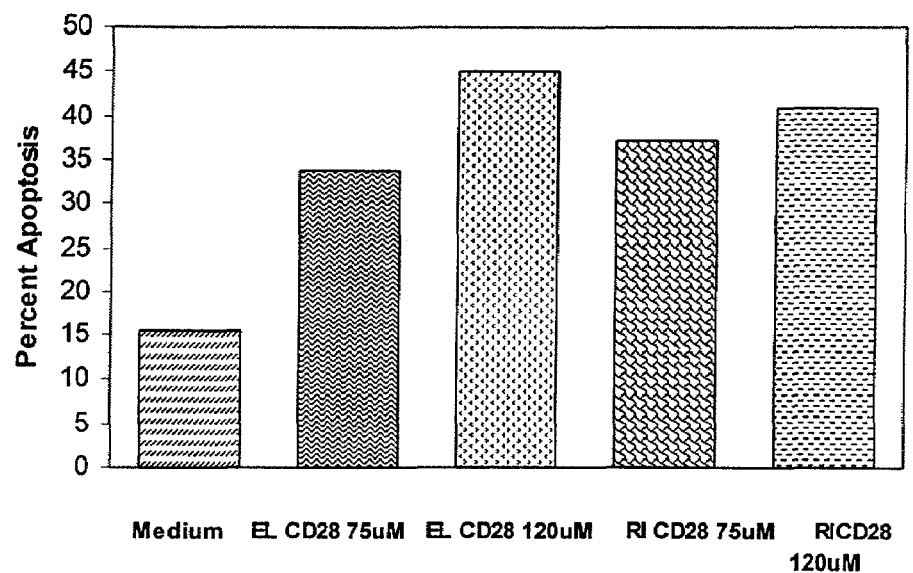
Figure 7B:
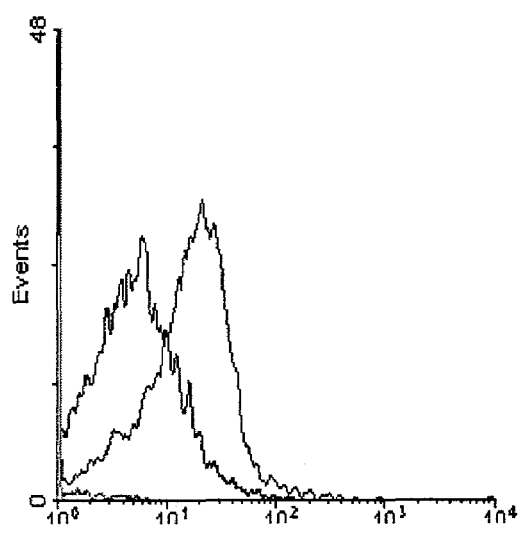
Figure 7C:
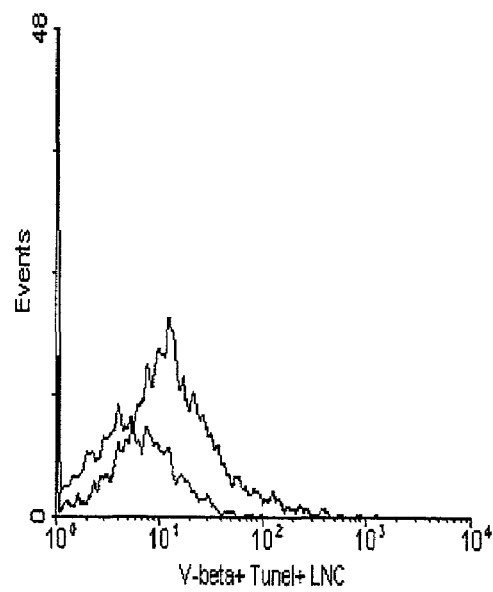

Treatment with 150 μM ELCD28 or RI CD28 peptides at the time of antigen stimulation resulted in a significantly higher percentage of antigen specific CD4+ LNC undergoing apoptosis after 48 hr culture when compared to untreated cells (15.4%) (FIG. 7). CD4+Vβ8.2+ spleen cells also exhibited increase in apoptosis when treated with 150 μM ELCD28 or RI CD28 peptide (data not shown).

FIG. 7a is a representative histogram of three different experiments showing increased apoptosis of the CD4+ LNC cultured in the presence of indicated CD28 APR. Control cells cultured in the absence of antigen were 80% apoptotic (data not shown). These results suggest that the synthetic CD28 effectively competes with cell surface CD28 for binding B7-ligands on the APC and blocks the costimulation required for sustained survival of antigen stimulated T-cells.

The functional efficacy in vitro, suggests a therapeutic potential for the CD28 peptide mimetics in various disease conditions requiring downregulation of T cell responses such as autoimmune diseases, certain chronic infections and graft-versus host disease.

Example 3

Treatment of EAE with the CD 28 Peptide Mimetics of Example 1

Most studies on costimulatory blockade in EAE have focused on the suppression of T cell responses during antigen priming and disease induction. In this Example, the ability of CD28 peptide mimetics to suppress ongoing clinical disease in EAE animals is demonstrated.

Mice:

Female B10.PL mice (6–8 wk old) were obtained from The Jackson laboratory (Bar Harbor, Me.) and housed at the Ohio State University, (Columbus, Ohio).

Induction of EAE and CD28 Peptide Treatment:

Mice were injected subcutaneously over four sites on the flank with an emulsion containing 200 μg of guinea-pig-MBP in CFA containing 200 μg heat killed *Mycobacterium tuberculosis*, Jamaica strain. Pertussis toxin (List Biological, Campbell, Calif.) at 150 ng in 0.2 ml of PBS was given intraperitoneally at the time of immunization and 48 hours later. Animals were observed daily for clinical signs and scored as follows: 1, limp tail or waddling gait with tail tonicity; 2, waddling gait with limp tail (ataxia); 2.5 ataxia with partial paralysis of one limb, 3, partial hind-limb paralysis, 3.5 full paralysis of one limb with partial paralysis of the second limb, 4, full paralysis of two limbs, 4.5 moribund and 5, death. All mice immunized with MBP (200 μg) in CFA developed clinical disease varying between ataxia and complete hind limb paralysis by day 14 post-immunization. They were then distributed randomly into six groups with mean clinical score of each group approximately the same.

Figure 8A:
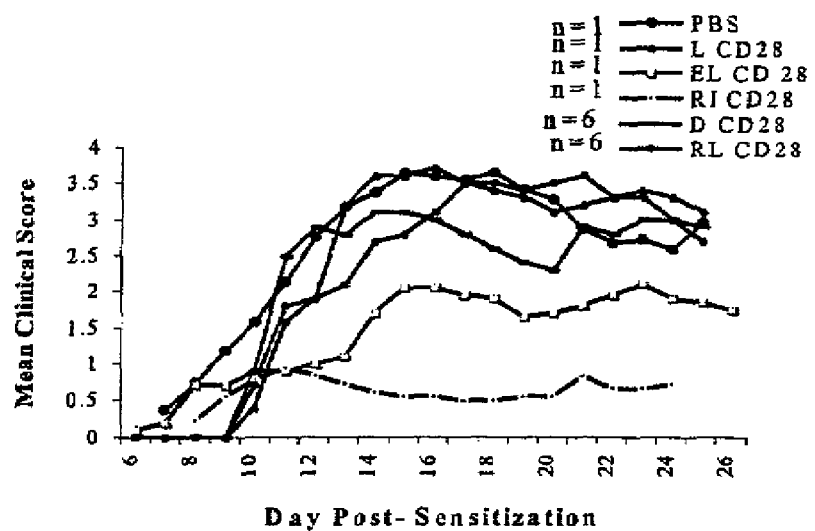

Groups of mice were left untreated or injected intravenously with 500 μg of EL CD28 or RI CD28 peptide mimetics, or LCD28, RLCD28 and DCD28 peptides. The mean clinical score of untreated mice continued to increase reaching a maximum of 3.4 on day 20. Similarly the disease continued to progress in mice treated with LCD28, RLCD28 and DCD28, reaching mean maximal clinical score of 3.8 (day 18), 3.4 (day 16 ) and 3.7 (day 16) respectively. In contrast mice treated with EL CD28 and RI CD28 peptide mimetics continued to show clinical improvement from day 16 throughout period of observation (26 days) post-immunization.(FIGS. 8A and B). This indicates that short-term blockade of CD28 costimulation was capable of attenuating ongoing disease progression in EAE.

The biological activity of synthetic CD28 peptide analogues during antigen priming in vivo in EAE was then shown. B10.PL mice immunized with GP-MBP (200 μg) in CFA were either left untreated or injected intravenously 500 μg of EL CD28 or RI CD28 peptide mimetics or LCD28, RLCD28 and DCD28 peptides on the day of immunization. The vehicle treated mice and mice treated with: LCD28, RL CD28 and D CD28 peptide had maximum disease incidence of 100%, 100%, 91.5% and 91.5% and maximum mean cumulative score per day of 1.9, 1.8, 1.7 and 2 respectively. In contrast, significant inhibition of EAE was observed with mean maximum incidence of 70% and 60% and a maximum mean cumulative score of 1.1 and 0.74 in mice treated with EL CD28 and RI CD28 peptide mimetics, respectively. The effect of RI CD28 peptide injection lasted for the duration of observation (37 days) in one experiment.

Figure 8B:
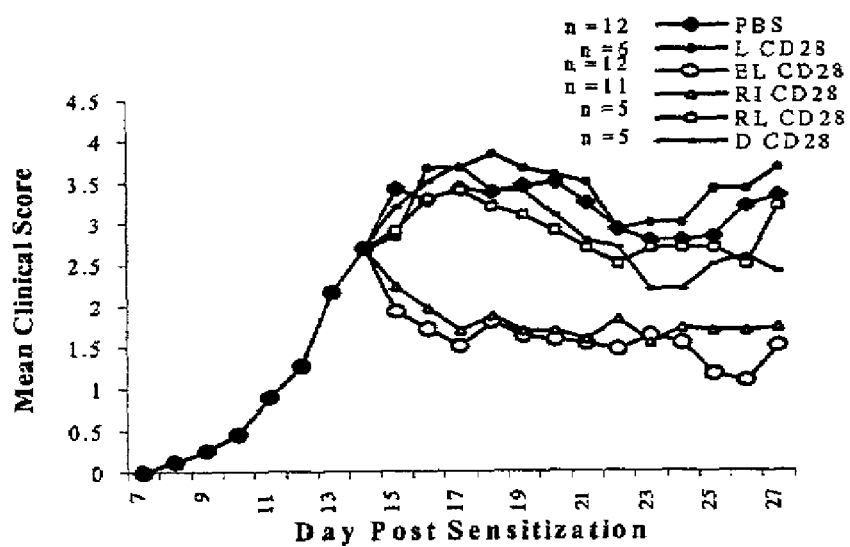

The data also show that single administration of synthetic CD28 peptide analogs ameliorated ongoing EAE in B10.PL mice. Groups of mice immunized with MBP in CFA were left untreated or injected intravenously 500 μg of EL CD28 or RI CD28 or control CD28 peptides on day 14, when most mice exhibited EAE with a minimal score of 2.0 (FIG. 8B)

Example 4

Treatment with Synthetic CD28 Peptide Mimetics Decreased IL-2 Production by Encephalitogenic T cells In Vivo MBP reactive T cells that induce EAE are known to display a $Th_1$ phenotype secreting the proinflammatory cytokines IL-2, TNF-γ and TNF-β (36. Kay, B. K., M. P. Williamson, and M. Sudol. 2000. *Faseb J* 14, no. 2:231). ELISPOT assay was used to assess in vitro cytokine production by draining lymph node cells and splenocytes upon restimulation from in vivo MBP-primed T cells. Mice were treated as described in Example 3, on day 0 of immunization. The frequency of IL-2 secreting lymph node cells decreased significantly EL-CD28 (2776+/−53.5; p<0.05) and RI CD28 (1753+/−37.7; p<0.01) treated mice as compared to vehicle (4846+/−14.3) and control RL-CD28 (3386+/−23.3) or D CD28 (2675+/−14.2) peptide treated mice.

Example 5

CD28 Peptide Mimetics Protect from EAE by Inducing Apoptosis of CD4+ T Cells In Vivo This study showed that the protective effects of CD28 peptide mimetics in EAE were mediated through apoptosis and quantified the effects. This was done by quantifying the DNA strand breaks in CD4+ lymphocytes detected by enzymatic labeling of nicked ends. Cells incubated in DNAse served as positive control. A significantly higher percentage of CD4+ T cells were apoptotic in mice treated with RI CD28 peptide mimetics (16%) on the day of immunization as compared to vehicle treated mice (8.7%).

What is claimed is:

1. A CD28 peptide mimetic for blocking deleterious T cell mediated immune reaction, said peptide mimetic being 20 to 25 amino acids in length, said peptide mimetic comprising levorotary or dextrorotary amino acids, wherein the peptide mimetic comprises the sequence set forth in SEQ. ID NO: 5 when the peptide mimetic comprises levorotary amino acids; and wherein the peptide mimetic comprises the sequence set forth in SEQ ID NO: 6 when the peptide mimetic comprises dextrorotary amino acids.

2. The peptide mimetic of claim 1 wherein the amino and carboxyl ends of the peptide are end blocked.

3. The peptide mimetic of claim 1, wherein the binding affinity of the peptide mimetic for the B7-1 protein is from 10 fold greater to 2 fold less than the binding affinity of CD 28 for the B7-1 protein.

4. The peptide mimetic of claim 1, wherein the binding affinity of the peptide mimetic for the B7-1 protein is less than the binding affinity of CTLA-4 for the B7-1 protein.

5. The peptide mimetic of claim 1, wherein the $K_d$ of the mimetic with respect to B7-1 is from 2 to 3 micromoles.

6. A CD28 peptide mimetic for blocking deleterious T cell mediated immune reaction, wherein said peptide mimetic is 20 or 21 amino acids in length and comprises levorotary or dextrorotary amino acids, and wherein the peptide mimetic comprises the sequence set forth in SEQ ID NO: 5 when the peptide mimetic comprises levorotary amino acids or the amino acid sequence set forth in SEQ ID NO: 6 when the peptide mimetic comprises dextrorotary amino acids.

7. The peptide mimetic of claim 6, wherein said peptide mimetic is 20 amino acids in length, and wherein the sequence of said peptide mimetic is SEQ ID NO: 5 or SEQ ID NO: 6.

* * * * *